United States Patent [19]

Wisnewski et al.

[11] Patent Number: 5,707,817

[45] Date of Patent: *Jan. 13, 1998

[54] CARBOHYDRATE-BASED VACCINE AND DIAGNOSTIC REAGENT FOR TRICHINOSIS

[75] Inventors: Nancy Wisnewski, Ft. Collins; Robert B. Grieve, Windsor; Donald L. Wassom; Michael R. McNeil, both of Ft. Collins, all of Colo.

[73] Assignee: Colorado State University Research Foundation, Ft. Collins, Colo.

[*] Notice: The term of this patent shall not extend beyond the expiration date of Pat. No. 5,541,075.

[21] Appl. No.: 415,365

[22] Filed: Mar. 31, 1995

Related U.S. Application Data

[63] Continuation-in-part of Ser. No. 14,449, Feb. 5, 1993, Pat. No. 5,541,075.

[51] Int. Cl.$^6$ .......................... G01N 33/569; A61K 31/70
[52] U.S. Cl. .......................... 435/7.22; 435/7.1; 514/25; 514/53; 514/61; 424/265.1
[58] Field of Search .......................... 435/7.1, 7.22; 514/25, 53, 61; 424/265.1

[56] References Cited

U.S. PATENT DOCUMENTS

| | | |
|---|---|---|
| 3,892,529 | 7/1975 | Giles . |
| 3,918,818 | 11/1975 | Giles . |
| 4,670,384 | 6/1987 | Gamble et al. . |
| 4,795,633 | 1/1989 | Murrell et al. . |
| 4,833,168 | 5/1989 | Wyvratt, Jr. . |
| 5,008,250 | 4/1991 | Fisher et al. . |
| 5,073,567 | 12/1991 | Kojima et al. . |
| 5,143,712 | 9/1992 | Brandley et al. . |
| 5,245,013 | 9/1993 | Ulevitch et al. . |
| 5,356,778 | 10/1994 | Hansen et al. . |
| 5,541,075 | 7/1996 | Wisnewski et al. . |

FOREIGN PATENT DOCUMENTS

| | | |
|---|---|---|
| 1 580 539 | 12/1980 | United Kingdom . |
| WO 89/00163 | 1/1989 | WIPO . |

OTHER PUBLICATIONS

Baumann et al., "Controlled Acid Hydrolysis of an O–Antigen Fragment Yields Univalent Heptasaccharide Haptens Containing One 3,6–dideoxyhexose Epitope", pp. 347–354, 1993, *Carbohydr. Res.*, vol. 247.

Bundle et al., "Molecular Recognition of a Salmonella Trisaccharide Epitope by Monoclonal Antibody Se 155–4", pp. 5172–5182, 1994, *Biochem.*, vol. 33.

Dick et al., "Glycoconjugates of Bacterial Carbohydrate Antigens", pp. 48–114, 1989, *Contrib. Microbiol. Immunol.*, vol. 10.

Ellis et al., "Glycans as Targets for Monoclonal Antibodies that Protect Rats Against *Trichinella spiralis*", pp. 585–592, 1994, *Glycobiol.*, vol. 2.

"Development of the Parasite", pp. 225–229, In *Parasitology and Parasitic Diseases of Livestock*, (V.S. Ershov, ed.), 1956.

Parkhouse et al., "Antigens of Parasitic Helminths in Diagnosis, Protection and Pathology", pp. S5–S19, 1989, *Parasitology*, vol. 99 Supplement.

Reason et al., "Novel Tyvelose–Containing Tri–and Tetra–Antennary N–glycans in the Immunodominant Antigens of the Intracellular Parasite *Trichinella spiralis*", pp. 593–603, 1994, *Glycobiol.*, vol. 4.

"Family Trichinellidae", pp. 454–459, In *Foundations of Parasitology*, 3rd Edition, (Schmidt et al., eds.) 1985.

Thorson et al., "Molecular Basis of 3,6–Dideoxyhexose Biosynthesis" Elucidation of CDP–Ascarylose Biosynthetic Genes and Their Relationship to Other 3,6–Dideoxyhexose Pathways, pp. 5827–5828, 1993, *J. Am Chem. Soc.*, vol. 115.

Appleton et al., "Consensus on *Trichinella spiralis* Antigens and Antibodies", pp. 190–192, 1991, *Parasitol. Today*, vol. 7.

Callahan et al., "*Dirofilaria immitis* Superoxide Dismutase: Purification and Characterization", pp. 245–252, 1991, *Mol. Biochem. Parasitol.*, vol. 49.

Carpenter, "Enzyme–Linked Immunoassays", pp. 2–9, 1992, *The Manual of Clinical Laboratory Immunology*, 4th Edition, Rose et al., eds., Am. Soc. of Microbiol., Washington, D.C.

Chaplin, "A Rapid and Sensitive Method for the Analysis of Carbohydrate Components in Glycoproteins Using Gas–Liquid Chromatography", pp. 336–341, 1982, *Anal. Biochem.*, vol. 123.

Cygler, et al., "Recognition of a Cell–Surface Oligosaccharide of Pathogenic Salmonella by an Antibody Fab Fragment", pp. 442–445, 1991, *Science*, vol. 253, Jul.

Denkers et al., "*Trichinella spiralis*: Influence of an Immunodominant, Carbohydrate–Associated Determinant on the Host Antibody Response Repertoire", pp. 403–410, 1991, *Exp. Parasitol.*, vol. 72.

Denkers et al., "The Mouse Antibody Response to *Trichinella spiralis* Defines a Single, Immunodominant Epitope Shared by Multiple Antigens", pp. 3152–3159, 1990, *J. Immunology*, vol. 144.

Denkers et al., "Characterization of *Trichinella spiralis* Antigens Sharing an Immunodominant, Carbohydrate–Associated Determinant Distinct from Phosphorylcholine", pp. 241–250, 1990, *Mol. Biochem. Parasitol.*, vol. 41.

Fairbairn, "The Biochemistry of Ascaris", pp. 491–554, 1957, *Exp. Parasitol.*, vol. 6.

Fairbairn and Passey, "The Lipid Components in the Vitelline Membrane of *Ascaris Lumbricoides* Eggs", pp. 130–134, 1954, *Can. J. Biochem. Physiol.*, vol. 33.

(List continued on next page.)

*Primary Examiner*—Paula K. Hutzell
*Assistant Examiner*—Khalid Masood
*Attorney, Agent, or Firm*—Sheridan Ross P.C.

[57] ABSTRACT

The present invention relates to Trichinella diagnostic reagents that include a β-tyvelose-containing composition and use of such reagents to detect Trichinella, and particularly *Trichinella spiralis* infections. The present invention also includes diagnostic kits based on such reagents and therapeutic agents based on the the knowledge that β-tyvelose is produced by *Trichinella spiralis* parasites.

25 Claims, No Drawings

OTHER PUBLICATIONS

Gamble et al., "Inoculation of Pigs Against *Trichinella Spiralis*, Using Larval Excretory–Secretory Antigens", pp. 2396–2399, 1986, *Am. J. Vet. Res.*, vol. 47, No. 11, Nov.

Gamble, "*Trichinella spiralis*: Immunization of Mice Using Monoclonal Antibody Affinity–Isolated Antigens", pp. 398–404, 1985, *Exp. Parasitol.*, vol. 59.

Gamble et al., "Comparison of Monoclonal Antibody–Based Competitive and Indirect Enzyme–Linked Immunosorbent Assays for the Diagnosis of Swine Trichinosis", pp. 379–389, 1984, *Vet. Immunol. Immunopathol.*, vol. 6.

Gamble et al., "Diagnosis of Swine Trichinosis by Enzyme–Linked Immunosorbent Assay (Elisa) Using an Excretory–Secretory Antigen", pp. 349–361, 1983, *Vet. Parasitol.*, vol. 13.

Gamble et. al., "Monoclonal Antibody–Purified Antigen for the Immunodiagnosis of Trichinosis", pp. 67–74, 1984, *Am. J. Vet. Res.*, vol. 45, Jan.

Gold et al., "Partial Characterization of two Antigens Secreted by $L_1$ Larvae of *Trichinella Spiralis*", pp. 187–196, 1990, *Mol. Biochem. Parasitol.*, vol. 41.

Hakomori, "A Rapid Permethylation of Glycolipid, and Polysaccharide Catalyzed by Methylsufinyl Carbanion in Dimethyl Sulfoxide", pp. 205–208, 1964, *J. Biochem.*, vol. 55.

Herrington et. al., "Safety and Immunogenicity in Man of a Synthetic Peptide Malaria Vaccine Against *Plasmodium Falciparum* Sporozoites", pp. 257–259, 1987, *Nature*, vol. 328, Jul.

Hey et. al., "Biosynthesis of Tyvelos", pp. 5473–5478, 1966, *J. Bio. Chem.*, vol. 241, Nov.

Iversen et al., "Antigenic Determinants of Salmonella Serogroups A and $D_1$ Synthesis of Trisaccharide Glycosides for Use as Artificial Antigens", pp. 29–40, 1982, *Carbohydr. Res.*, vol. 103.

Jezyk et. al., "Ascarosides and Ascaroside Esters in *Ascaris Lumbricoides* (Nematoda)", pp. 691–705, 1967 *Comp. Biochem. Physiol.*, vol. 23.

Jezyk et. al., "Metabolism of Ascarosides in the Ovaries of *Ascaris Lumbricoides* (Nemotoda)", pp. 707–719, 1967, *Comp. Biochem. Physiol.*, vol. 23.

Jörbeck, et al., "Immunochemistry of Salmonella O–Antigens", pp. 11–19, 1979, *Int. Archs Allergy appl. Immun.*, vol. 58.

Jörbeck, et al., "Artificial Salmonella Vaccines: *Salmonella typhimurium* O–Antigen–Specific Oligosaccharide–Protein Conjugates Elicit Opsonizing Antibodies that Enhance Phagocytosis", pp. 497–502, 1981, *Infect. Immun.*, vol. 32, No. 2, May.

Kabat, "Antibody (and Lectin) Combining Sites for Elucidating Structures; Inhibition Reactions for Elucidating Structures", pp. 176–179, 1976, *Sturctural Concepts in Immunology and Immunochemistry*, (Holt, Rinehart and Winston, NY).

Leontein et al., "Assignment of Absolute Configuration of Sugars by G.L.C. of their Acetylated Glycosides Formed From Chiral Alcohols", pp. 359–362, 1978, *Carbohydr. Res.*, vol. 62.

Lindberg et. al., "Immunology and Immunochemistry of Synthetic and Semisynthetic Salmonella O–Antigen–Specific Glycoconjugates", pp. 83–118, 1983, in *Bacterial Lipopolysaccahrides—Structure, Synthesis and Biological Activities*, L. Anderson and F.M. Unger, eds., ACS Symposium Series, Wash. D.C.

Lindberg, et al., "Structural Studies of the O–Specific Side–Chain of the Lipopolysaccharide From *Escherichia coli* O 55", pp. 105–112, 1981, *Carbohydr. Res.*, vol. 97.

Lu, et al., "Characterization and Application of a Murine Monoclonal Antibody that Reacts Specifically With the Serogroup $D_1$ Salmonella", pp. 135–140, 1991, *FEMS Microbiology Letters*, vol. 80.

Lüderitz et. al., "Immunochemistry of O and R Antigens of Salmonella and Related Enterobacteriaceae", pp. 192–255, 1966, *Bacteriological Rev.*, vol. 30.

Matsuhashi et. al., "Enzymatic Synthesis of Cytidine Diphosphate 3,6–Dideoxyhexoses", pp. 4267–4274, 1966, *J. Biol. Chem.*, vol. 241.

Matsuhashi, "Enzymatic Synthesis of Cytidine Diphosphate 3,6–Dideoxyhexoses", pp. 4275–4282, 1966, *J. Biol. Chem.*, vol. 241.

Matsuhashi et. al., "Enzymatic Synthesis of Cytidine Diphosphate 3,6–Dideoxyhexoses", pp. 4283–4287, 1966, *J. Biol. Chem.*, vol. 241.

McBroom et. al., "Carbohydrate Antigens: Coupling of Carbohydrates to Proteins by Diazonium and Phenylisothiocyanate Reactions", pp. 212–219, 1972, *Meth. Enzymol.*, vol. 28B.

Ruitenberg et. al., "Reliability of the Enzyme–Linked Immunosorbent Assay (Elisa) for the Serodiagnosis of *Trichinella Spiralis* Infections in Conventionally Raised Pigs", pp. 67–83, 1976, *J. of Immunol. Meth.*, vol. 10.

Russell et. al., "Synthesis of Stereospecifically Labeled 3,6–Dideoxyhexoses", pp. 95–114, 1990, *Carbohydrate Res.*, vol. 201.

Samuelsson, et al., "Structure of O–Specific Side Chains of Lipopolysaccharides from *Yersinia pseudotuberculosis*", pp. 1010–1016, 1974, *J. Bateriol.*, vol. 117, No. 3, Mar.

Sanford et. al., "The Structure of the *Aerobacter Aerogenes* A3 (SI) Polysaccharide. I. A Reexamination Using Improved Procedures for Methylation Analysis", pp. 1508–1517, 1966, *Biochem.*, vol. 5, May.

Silberstein et. al., "Antigens from *Trichinella Spiralis* That Induce a Protective Response In The Mouse", pp. 898–904, 1984, *J. Immunol.*, vol. 132, Feb.

Silberstein et. al., "Immunization With Purified Antigens Protects Mice From Lethal Infection With *Trichinella Spiralis*", pp. 516–517, 1985, *J. Parasitol.*, vol. 71, Aug.

Su et. al., "A Dot–Elisa Mimicry Western Blot Test for the Detection of Swine Trichinellosis", pp.76–82, 1991, *J. Parasitol.*, vol. 77.

Su et al., "Cloning and Expression of Complementary DNA Encoding an Antigen of *Trichinella Spiralis*", pp. 331–336, 1991, *Mol. Biochem. Parasitol.*, vol. 45.

Sugane et. al., "Molecular Analysis of the Gene Encoding an Antigenic Polypeptide of *Trichinella Spiralis* Infective Larvae", pp. 1–8, 1990, *J. Helminthol.*, vol. 64.

Svenson et. al., "Coupling of Acid Labile Salmonella Specific Oligosaccharides to Macromolecular Carriers", pp. 323–335, 1979, *J. Immunol. Meth.*, vol. 25.

Svenson et al., "Artificial Salmonella Vaccines: *Salmonella typhimurium* O–Antigen–Specific Oligo–Saccharide–Protein Conjugates Elicit Protective Antibodies in Rabbits and Mice", pp. 490–496, 1981, *Infect. Immun.*, vol. 32, No. 1, May.

Svenson et al., "Artificial Salmonella Vaccines: O–Antigenic Oligosaccharide–Protein Conjugates Induce Protection Against Infection with *Salmonella typhimurium*", pp. 863–872, 1979, *Infect. Immun.*, vol. 25, No. 3, Sep.

Svenugsson et. al., "Synthetic Disaccharide—Protein Antigens for Production of Specific 04 and 09 Antisera for Immunofluorescence Diagnosis of Salmonella", pp. 1–11, *Med. Microbiol. Immunol.*, vol. 163.

Svenungsson, et al., "Diagnosis of Salmonella Infections: Specificity of Indirect Immunofluorescence for Rapid Identification of *Salmonella enteritidis* and Usefulness of Enzyme–Linked Immunosorbent Assay", pp. 927–936, 1979, *J. Infect. Dis.*, vol. 140, No. 6, Dec.

Verma et. al., "Identification and Sequence of rfbS and rfbE, Which Determine Antigenic Specificity of Group A and Group D Salmonellae", pp. 5694–5701, 1989, *J. Bacteriol.*, vol. 171, Oct.

Waeghe et. al., "Determination, by Methylation Analysis, of the Glycosyl–Linkage Compositions of Microgram Quantities of Complex Carbohydrates", pp. 281–304, 1983, *Carb. Res.*, vol. 123.

Wyk et. al., "Identification and Sequence of the Gene for Abequose Synthase, Which Confers Antigenic Specificity on Group B Salmonellae: Homology With Galactose Epimerase", pp. 5687–5693, 1989, *J. Bacteriol.*, vol. 171, Oct.

York et. al., "Isolation and Characterization of Plant Cell Walls and Cell Wall Components", pp. 3–40, 1985, *Meth. Enzymol.*, vol. 118.

Zarlenga et al., "Molecular Cloning and Expression of an Immunodominant 53–kDa Excretory–Secretory Antigen From *Trichinella Spiralis* Muscle Larvae", pp. 165–174, 1990, *Mol. Biochem. Parasitol.*, vol. 42.

Carlsson et. al. (1978) Acta Path. Microbiol. Scand. Sec. C. 86, 237–244.

Takata et. al. (1987) J. of Leukocyte Biol. vol. 41, 248–256.

Olson et al, J. of Medicinal Chemistry 36(21):3039–3049, 1993.

Moore et al, Trends Pharmacol Sci 15(4):124–129, 1994.

CARBOHYDRATE-BASED VACCINE AND DIAGNOSTIC REAGENT FOR TRICHINOSIS

CROSS REFERENCE TO RELATED APPLICATIONS

The present application is a continuation-in-part of U.S. patent application Ser. No. 08/014,449 for "Carbohydrate-based Vaccine and Diagnostic Reagent for Trichinosis", filed Feb. 5, 1993, (now U.S. Pat. No. 5,541,075) incorporated herein by this reference in its entirety.

FIELD OF THE INVENTION

The present invention relates to novel carbohydrate-based vaccines and their use to protect animals from Trichinella infection. The present invention further relates to novel carbohydrate-based diagnostic reagents and their use to detect Trichinella infection in animals. The invention particularly relates to β-tyvelose-containing vaccines to protect animals from trichinosis and to β-tyvelose-containing diagnostic reagents to detect Trichinella spiralis infection.

BACKGROUND OF THE INVENTION

Trichinosis is a disease of world-wide distribution that is primarily due to the ingestion of raw or undercooked meat (principally pork) containing the infective larval stage of Trichinella spiralis (T. spiralis), the helminth parasite that causes the disease. After ingestion, T. spiralis larvae infect the intestine where they mature within a few days. Female worms then bear newborn larvae which enter the general circulatory system and after several days accumulate in the striated muscles of the infected animal. Until recently, T. spiralis infection has been detected by visual detection of larvae in muscle snips or digestion of muscle to liberate larvae (see, for example, U.S. Pat. No. 3,892,529 by Giles, issued Jul. 1, 1975, and U.S. Pat. No. 3,918,818 by Giles, issued Nov. 11, 1975).

A group of protein (including glycoprotein) antigens extracted from T. spiralis muscle stage larvae has been the subject of numerous studies in recent years, particularly in attempts to develop vaccines and diagnostic agents for trichinosis. These larval antigens are highly immunodominant and are apparently only present during the first muscle larval stage ($L_1$) of T. spiralis infection, being found on both the cuticular surface and excretory/secretory (ES) products of $L_1$ larvae (see, for example, Denkers et al., pp. 241–250, 1990, Mol. Biochem. Parasitol., Vol. 41). These larval antigens, designated TSL-1 antigens by Appleton et al., pp. 190–192, 1991, Parasitol. Today, Vol. 7, evoke a strong $IgG_1$ antibody response in mice following oral infection (see, for example, Denkers et al., pp. 3152–3159, 1990, J. Immunol., Vol. 144) and induce substantial protection against challenge infections (see, for example, Silberstein et al., pp. 898–904, 1984, J. Immunol., Vol. 132; Silberstein et al., pp. 516–517, 1985, J. Parasitol., Vol. 71; Gamble, pp. 398–404, 1985, Exp. Parasitol., Vol. 59; Gamble et al., pp. 2396–2399, 1986, Am. J. Vet. Res., Vol. 47; Ortega-Pierres et al., pp. 563–567, 1989, Parasitol. Res., Vol. 75; Denkers et al., J. Immunol., ibid.; Jarvis et al., pp. 498–501, 1992, Parasite Immunol., Vol. 14).

TSL-1 antigens migrate under reducing conditions on SDS-PAGE (sodium dodecyl sulfate polyacrylamide gel electrophoresis) in a molecular weight range of 40–70 kilodaltons (kD). Denkers et al., Mol. Biochem. Parasitol., ibid., have shown that at least six of the TSL-1 antigens share a common, highly immunodominant determinant. Use of monoclonal antibodies raised against the determinants indicate that the determinants are quite selective for T. spiralis in that the monoclonal antibodies do not recognize other parasites, including the closely related species Trichuris muris (Denkers et al., pp. 403–410, 1991, Exp. Parasitol., Vol. 72). Moreover, the determinants appear to be ubiquitous among all T. spiralis isolates tested so far (see, for example, Denkers et al., Exp. Parasitol., ibid.; Gamble et al., pp. 67–74, 1984, Am. J. Vet. Res., Vol. 46; Gamble et al., pp. 379–389, 1984, Vet. Immunol. Immunopath., Vol. 6).

TSL-1 antigens are believed to have both protein and carbohydrate immunoreactive determinants, although there is some conflict in the literature about the importance of each. Denkers, et al., Mol. Biochem. Parasitol., ibid., demonstrated that the immunodominant determinants can be removed by treatment with trifluoromethanesulfonic acid, mild base, or N-glycanase, suggesting that the determinants are associated with both N-linked and O-linked carbohydrate groups. Denkers et al. also showed that the immunodominant determinants were not phosphorylcholine but did not further identify the composition of the carbohydrate moiety. Gold et al., pp. 187–196, Mol. Biochem. Parasitol., Vol. 41, isolated TSL-1 antigens of 43 kd and 45–50 kd and treated them with N-glycanase. The deglycosylated antigens were no longer able to bind to polyclonal antibodies raised against the glycosylated versions of the proteins, again suggesting the importance of carbohydrate moieties, although Gold et al. do not exclude the possibility of peptide epitopes as well.

In contrast, Jarvis et al., ibid., concluded that protein epitopes alone could induce protective immunity to T. spiralis, having shown that ES antigens that had been deglycosylated using sodium periodate were as effective as native ES antigens in protecting mice from T. spiralis infection in both active and passive immune assays. Su et al., pp. 331–336, 1991, Mol. Biochem. Parasitol., Vol. 45, reported that a recombinant fusion protein consisting of β-galactosidase joined to the 49-kd TSL-1 antigen (P49) produced in Escherichia coli was bound by antibodies contained in serum isolated from swine infected with T. spiralis, and by antibodies contained in serum isolated from mice immunized with native P49 antigen, but was not recognized by three monoclonal antibodies that bind selectively to native P49 antigen. Su et al. concluded that such results suggest that, at least the P49 antigen has both protein and carbohydrate immunoreactive determinants.

Several investigators have developed enzyme-linked immunosorbent assays (ELISAs) to detect T. spiralis infection using a variety of reagents, such as, crude T. spiralis parasite preparations, partially purified ES antigen preparations, and monoclonal antibodies raised against, for example, the ES immunodominant determinants (see, for example, Ruitenberg et al., pp. 67–83, 1976, J. Immunol. Methods, Vol. 10; Gamble et al., 1983, pp. 349–361, Vet. Parasitol., Vol. 13; Gamble et al., Am. J. Vet. Res., ibid.; Gamble et al., Vet. Immunol. Immunopath., ibid.; U.S. Pat. No. 4,670,384, by Gamble et al., issued Jun. 2, 1987). Assays based on undefined crude or semi-defined antigen preparations are problematic due to false-positive and false-negative reactions as well as to cross-reactivity with antibodies corresponding to antigens of other parasites. Monoclonal antibody-based or purified protein-based assays, while often leading to fewer false-positive or false-negative reactions, can still have specificity and selectivity problems, in addition to difficulties of producing such components without batch-to-batch variation, and of maintaining the stability of the components.

U.S. Pat. No. 4,795,633, by Murrell et al., issued Jan. 3, 1989, discloses a swine trichinosis vaccine consisting of an inert newborn larvae preparation emulsified with an adjuvant. GB 1,580,539, published Dec. 3, 1989, discloses a trichinosis vaccine containing ES antigens of $T.$ $spiralis$ muscle stage larvae. Several investigators have reported the cloning of at least portions of certain $T.$ $spiralis$ antigen genes with the goal of developing defined diagnostics reagents and/or vaccines (see, for example, Su et al., $Mol.$ $Biochem.$ $Parasitol.$, ibid.; Sugane et al., pp. 1–8, 1990, $J.$ $Helminth.$, Vol. 64; Zarlenga et al., pp. 165–174, 1990, $Mol.$ $Biochem.$ $Parasitol.$, Vol. 42). Problems with protein-based vaccines, and particularly with recombinant protein-based vaccines, include difficulty of preparation (particularly with respect to removal of harmful contaminants), lack of stability, potential reduced antigenicity compared to the native protein, and potential autoimmune reactions due to similarities between parasite and animal host proteins.

A number of anthelminthic drugs have been developed to treat trichinosis (see, for example, U.S. Pat. No. 5,140,042 by Arison et al., issued Aug. 18, 1992; U.S. Pat. No. 5,089,530 by Tsipouras et al., issued Feb. 18, 1992; U.S. Pat. No. 5,073,567, by Maeda et al., issued Dec. 17, 1991; U.S. Pat. No. 5,008,250, by Fisher et al., issued Apr. 16, 1991; and U.S. Pat. No. 4,833,168, by Wyvratt, issued May 23, 1989). Such drugs, however, apparently cannot be used to prevent trichinosis, are expensive to produce, usually have undesirable side effects, and are not always effective.

There remains a need for both diagnostic reagents to detect $T.$ $spiralis$ infection and for vaccines and other drugs to protect animals from trichinosis that have improved specificity, selectivity, stability, consistency, and ease of use.

SUMMARY OF THE INVENTION

The present invention relates to β-tyvelose-based vaccines and diagnostic reagents and their use to, respectively, protect against and detect Trichinella, and preferably $T.$ $spiralis$, infection.

One embodiment of the present invention is a vaccine that, when administered to an animal, protects that animal from Trichinella infection. Such a vaccine includes a β-tyvelose-containing composition or mimetope thereof and preferably also includes a pharmaceutically acceptable excipient. A β-tyvelose-containing composition of the present invention includes β-tyvelose or β-tyvelose joined through glycosidic linkage to at least one monosaccharide to form an oligosaccharide having at least one tyvelose terminal residue. Preferred vaccines contain β-tyvelose-containing disaccharides, trisaccharides, or tetrasaccharides. Particularly preferred β-tyvelose-containing compositions include those in which β-tyvelose is joined to N-acetylgalactosamine through glycosidic linkage. A preferred embodiment is a vaccine that includes a β-tyvelose-containing composition conjugated to an effective carrier. The present invention also includes a method to use such vaccines to protect an animal from Trichinella infection.

The present invention furthermore relates to diagnostic reagents effective in detecting Trichinella infection, and preferably $T.$ $spiralis$ infection. Such diagnostic reagents include a β-tyvelose-containing composition or mimetope thereof of the present invention. The present invention also include diagnostic kits including such diagnostic reagents and means to detect Trichinella infection.

Another embodiment of the present invention is a method to determine Trichinella, and preferably $T.$ $spiralis$, infection in an animal which includes (a) contacting a bodily fluid collected from the animal with a diagnostic reagent comprising a β-tyvelose-containing composition or mimetope thereof of the present invention to form an immunocomplex; and (b) determining Trichinella infection by detecting the immunocomplex formed in step (a), in which the presence of the immunocomplex indicates Trichinella infection.

Another embodiment of the present invention is a preparation of one or more antibodies capable of selectively binding to a Trichinella parasite, a preparation of such antibodies being produced by a process that includes the steps of (a) administering to an animal an effective amount of a composition comprising a β-tyvelose-containing composition or mimetope thereof of the present invention, and (b) recovering antibodies produced by the animal in response to administering the composition. Such a preparation of antibodies can be used to protect an animal from Trichinella infection, such as from trichinosis, by administering to the animal an amount of the preparation effective to protect the animal from trichinosis. Such antibodies can also be used to diagnose Trichinella infection in an animal.

An additional embodiment is a therapeutic agent capable of inhibiting a Trichinella enzyme of the β-tyvelose biosynthetic pathway, whereby the agent protects an animal from trichinosis. Methods to use such therapeutic agents are also included in the present invention.

DETAILED DESCRIPTION OF THE INVENTION

The present invention includes vaccines and diagnostic reagents, preferably directed against Trichinella, and even more preferably directed against $T.$ $spiralis$, infection, that contain β-tyvelose (i.e., β-3,6-dideoxy-D-arabinohexose). Related patent application U.S. patent application Ser. No. 08/014,449 (also referred to herein as Ser. No. 08/014,449, and which has published as PCT Publication No. WO 94/17824, by Wisnewski et al., publication date of Aug. 18, 1994), ibid., reports the discovery that the immunodominant antigen, TSL-1, of $T.$ $spiralis$ contains significant amounts of tyvelose, a sugar rarely found in nature. The inventors of the present invention have now discovered that the particular glycan epitope that is an immunodominant determinant of TSL-1 antigen contains β-tyvelose as a terminal residue. The inventors are not aware of any organism other than Trichinella that contain β-tyvelose epitopes. Other tyvelose-containing organisms (i.e., Salmonella serogroup $D$ or $Yersinia$ $pseudotuberculosis$ serogroup IV microorganisms) contain α-tyvelose epitopes. Thus, the vaccines and diagnostic reagents of the present invention are particularly advantageous because they are highly selective for Trichinella, and particularly for $T.$ $spiralis$ infection.

While the inventors have discovered that β-tyvelose is a preferred immunodominant epitope, the inventors have also discovered that α-tyvelose can also function, albeit to a much lesser extent, having from about 1 percent to about 10 percent the activity of β-tyvelose. As such, α-tyvelose can be included in vaccines and diagnostic reagents of the present invention. In one embodiment, for example, vaccines of the present invention include racemic mixtures of α- and β-tyvelose, either alone or joined to one or more monosaccharides and/or carriers. Such racemic mixtures are commercially valuable because they are less expensive to prepare than homogenous compositions of α- or β-tyvelose.

The inventors have also identified, in Ser. No. 08/014,449, ibid., four other monosaccharides that comprise a substantial proportion of $T.$ $spiralis$ TSL-1 immunodominant determinants: fucose, mannose, N-acetylgalactosamine, and N-acetylglucosamine, with the amount of fucose present being surprisingly high. Fucose, although prevalent in nature, is not usually a dominant sugar in the overall composition. Fucose has also been shown to have immunological relevance in mammals and parasites, having been found associated with several particular parasites and with glycosphingolipids in certain mammalian tumor tissues. As such, fucose-based vaccines of the present invention are also believed to be advantageous for protecting an animal from trichinosis. Using the information provided in Ser. No. 08/014,449, ibid., Reason et al., in 1994, *Glycobiology* 4, 593–603, deduced the structure of TSL-1 immunodominant glycan epitopes, verifying that tyvelose and fucose are terminal residues and indicating how tyvelose, fucose, mannose, N-acetylgalactosamine and N-acetylglucosamine are linked. Reason et al., however, did not report which isoform of tyvelose was present on the TSL-1 antigen.

One embodiment of the present invention is a vaccine that when administered to an animal, protects the animal from Trichinella infection, the vaccine comprising a β-tyvelose-containing composition or mimetope thereof, preferably in admixture with a pharmaceutically acceptable excipient. As used herein, a β-tyvelose-containing composition includes β-tyvelose and/or β-tyvelose joined through glycosidic linkage to at least one monosaccharide to form an oligosaccharide having at least one β-tyvelose terminal residue. As used herein, the terms "a", "at least one" and "one or more" can be used interchangeably. For example, the phrase "a composition" refers to at least one composition.

As used herein, a vaccine that "protects an animal from Trichinella infection" refers to the ability of the vaccine to treat (e.g., as an immunotherapeutic agent), ameliorate, and/or prevent Trichinella infection caused by a Trichinella parasite that contains β-tyvelose antigenic epitopes (i.e., epitopes that are able to bind to antibodies produced upon administration of a β-tyvelose-containing composition of the present invention). As used herein, a vaccine that protects an animal from trichinosis" refers to the ability of the vaccine to treat (e.g., as an immunotherapeutic agent), ameliorate, and/or prevent *T. spiralis* infection that otherwise would lead to trichinosis in the animal. Preferably the vaccine protects the animal by eliciting an immune response. A preferred vaccine is one that, when administered to an animal, is able to elicit (i.e., stimulate) the production of high antibody titers as well as a high-level cellular immune response capable of protecting the animal from trichinosis.

As used herein, "tyvelose joined through glycosidic linkage to at least one of the following monosaccharides" denotes an oligosaccharide in which β-tyvelose is joined to one or more monosaccharides according to standard carbohydrate chemistry (i.e., by glycosidic linkages). As such, the oligosaccharide can be either linear or branched. An oligosaccharide can be as small as a disaccharide and can be as large as is useful in the present invention, including as large as the natural oligosaccharide determinants on TSL-1 antigens.

The inventors have found that β-tyvelose is located predominantly, if not entirely, at the non-reducing terminal position of TSL-1 immunodominant determinants; i.e., that β-tyvelose is believed to be principally a terminal residue of naturally-occurring oligosaccharides on TSL-1 antigens. As used herein, a "terminal residue" is located either at an end (terminus) of or at a branch-point of an oligosaccharide such that the residue is exposed to elicit an immune response capable of protecting an animal from trichinosis and/or to bind (i.e., adsorb) selectively to an antibody indicative of *T. spiralis* infection.

Preferred monosaccharides in a β-tyvelose-containing composition include tyvelose (Tyv), fucose (Fuc), mannose (Man), N-acetylgalactosamine (N-Gal), and/or N-acetylglucosamine (N-Glc). A particularly preferred β-tyvelose-containing composition is an oligosaccharide in which β-tyvelose is attached by glycosidic linkage to N-Gal. Such a composition can be a disaccharide, trisaccharide, tetrasaccharide, or larger oligosaccharide. Such a composition can be linear or branched, with one or more branches such that β-tyvelose residues in the oligosaccharide are preferably terminal residues.

It is within the scope of the invention that those compositions produced using β-tyvelose, also can be produced using α-tyvelose. For example, an α-tyvelose-containing composition of the present invention can comprise α-tyvelose and α-tyvelose joined through glycosidic linkage to at least one monosaccharide to form an oligosaccharide having at least one α-tyvelose terminal residue. Such an α-tyvelose-containing composition can include a pharmaceutically acceptable excipient. As such, vaccines of the present invention can include racemic mixtures of β-tyvelose-containing compositions and α-tyvelose-containing compositions of the present invention, preferably in admixture with a pharmaceutically acceptable excipient.

In accordance with the present invention, a "mimetope" refers to any compound that is able to mimic the ability of an isolated composition of the present invention. A mimetope can be a compound that has been modified to decrease its susceptibility to degradation but that still retains the ability to stimulate antibody production or bind to an antibody specific for a composition of the present invention. Examples of mimetopes include, but are not limited to, protein-based compounds, carbohydrate-based compounds, lipid-based compounds, nucleic acid-based compounds, natural organic compounds, synthetically derived organic compounds, anti-idiotypic antibodies and/or catalytic antibodies, or fragments thereof. A mimetope can be obtained by, for example, screening libraries of natural and synthetic compounds for compounds capable of protecting an animal from Trichinella infection when administered in an effective amount or capable of selectively binding to an antibody indicative of Trichinella infection, as disclosed herein. A mimetope can also be obtained by, for example, rational drug design. In a rational drug design procedure, the three-dimensional structure of a composition of the present invention can be analyzed by, for example, nuclear magnetic resonance (NMR) or x-ray crystallography. The three-dimensional structure can then be used to predict structures of potential mimetopes by, for example, computer modelling. The predicted mimetope structures can then be produced by, for example, chemical synthesis, recombinant DNA technology, or by isolating a mimetope from a natural source (e.g., plants, animals, bacteria and fungi).

One embodiment of the present invention is a vaccine that includes not only a β-tyvelose-containing composition but also a fucose-containing composition or a mimetope thereof. A fucose-containing composition of the present invention can be fucose or fucose joined through glycosidic linkage to at least one monosaccharide to form an oligosaccharide having at least one fucose terminal residue. Preferred monosaccharides in a fucose-containing composition include tyvelose, fucose, mannose, N-acetylgalactosamine, and N-acetylglucosamine. A particularly preferred fucose-containing composition is one in which fucose is joined through glycosidic linkage to N-acetylglucosamine. Such a composition can be a disaccharide, trisaccharide, tetrasaccharide or larger oligosaccharide. Such a composition can be linear or branched, with one or more branches such that fucose residues in the oligosaccharide are preferably terminal residues.

As used herein, a mimetope of a fucose-containing composition is a molecule (e.g., a carbohydrate or other organic molecule) that has an epitope that can essentially mimic the fucose-containing composition's epitope by eliciting a substantially similar immune response. Preferably the mimetope has a similar tertiary structure to the fucose-containing composition's epitope. As such, mimetopes of fucose may be determined in manners as disclosed herein.

Suitable β-tyvelose-containing compositions of the present invention include β-tyvelose, and β-tyvelose joined to any number of monosaccharides to form a linear or branched structure, preferably in such a manner that β-tyvelose residues in the oligosaccharide are terminal residues. Preferred β-tyvelose-containing compositions include those in which β-tyvelose is joined to from about one to about three monosaccharides. More preferred β-tyvelose-containing compositions include β-tyvelose-containing disaccharides, trisaccharides and tetrasaccharides. Similarly, Suitable α-tyvelose-containing compositions of the present invention include α-tyvelose, and α-tyvelose joined to any number of monosaccharides to form a linear or branched structure, preferably in such a manner that α-tyvelose residues in the oligosaccharide are terminal residues. Preferred α-tyvelose-containing compositions include those in which α-tyvelose is joined to from about one to about three monosaccharides. More preferred α-tyvelose-containing compositions include α-tyvelose-containing disaccharides, trisaccharides and tetrasaccharides. Furthermore, suitable fucose-containing compositions of the present invention include fucose, and fucose joined to any number of monosaccharides to form a linear or branched structure, preferably in such a manner that fucose residues in the oligosaccharide are terminal residues. Preferred fucose-containing compositions include those in which fucose is joined to from about one to about three monosaccharides. More preferred fucose-containing compositions include fucose-containing disaccharides, trisaccharides and tetrasaccharides. It is also within the scope of the invention that larger oligosaccharides having at least one β-tyvelose terminal residue and/or at least one fucose terminal residue can also be effective vaccines.

Particularly preferred vaccines of the present invention include one or more of the following oligosaccharides: β-Tyv--Tyv, β-Tyv--Fuc, β-Tyv--Man, β-Tyv--N-Gal, β-Tyv--N-Glc, β-Tyv--N-Gal--N-Glc,

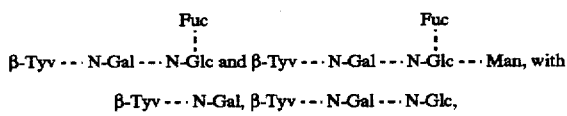

being even more preferred. Such preferred vaccines can also include one or more of the corresponding α-tyvelose-containing compositions. One class of preferred vaccines also includes one or more of the following fucose-containing compositions: Fuc--Fuc, Fuc--Tyv, Fuc--Man, Fuc--N-Gal and Fuc--N-Glc, with Fuc--N-Glc being particularly preferred. As used herein "--" in this context indicates the glycosidic linkage that forms the oligosaccharide.

Without being bound by theory, the inventors believe that oligosaccharide vaccines against trichinosis can be equally effective as oligosaccharide vaccines against Salmonella, which are described, for example, in Svenungsson et al., pp. 1-11, 1977, *Med. Microbiol. Immunol.*, Vol. 163; in Lindberg et al., ibid..; and in references cited therein. The inventors further believe that tyvelose particularly is likely to make an effective vaccine since tyvelose, like other 3,6-dideoxyhexoses, is a dominant antigenic determinant.

A preferred embodiment of the present invention is a vaccine that includes a composition of the present invention conjugated to an effective carrier. As used herein, an effective carrier is a compound that enables the composition to function as a vaccine or diagnostic agent and that is conjugated to the composition in such a manner as to not substantially interfere with the composition's desired function. Preferably, the carrier is able to augment, or enhance, the composition's activity as a vaccine or diagnostic reagent. As used herein, "conjugated" refers to joining the carbohydrate moiety and carrier together, preferably by a covalent attachment. For example, a β-tyvelose-containing composition is attached to a carrier in such a manner that the β-tyvelose epitope maintains the capacity to elicit an immune response capable of protecting an animal from trichinosis or to selectively bind to an antibody indicative of *T. spiralis* infection. When the β-tyvelose-containing composition is a disaccharide or larger oligosaccharide, the carrier is typically attached to a monosaccharide other than the β-tyvelose epitope in order to reduce potential interference with the ability of the oligosaccharide to function as an effective vaccine or diagnostic reagent. Particularly preferred vaccines include β-Tyv::carrier, β-Tyv--Tyv::carrier, β-Tyv--Fuc::carrier, β-Tyv--Man::carrier, β-Tyv--N-Gal::carrier, β-Tyv--N-Glc::carrier, β-Tyv--N-Gal--N-Glc::carrier,

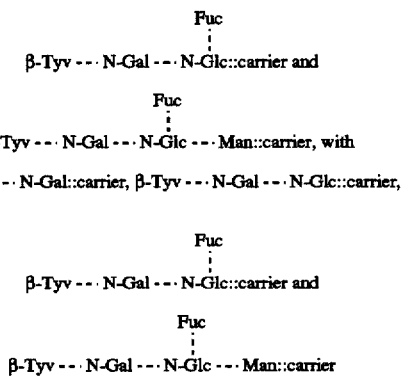

being even more preferred wherein "::" indicates the attachment of the carrier to the oligosaccharide. Certain preferred vaccines are racemic mixtures in which α-tyvelose-containing compositions are also attached to a carrier and/or also contain one or more fucose-containing compositions attached to a carrier.

A preferred carrier is a compound of sufficient size and immunogenicity capable of augmenting the immune response of the vaccine. Suitable carriers include, but are not limited to: proteins, such as toxoids, serum proteins, keyhole limoet hemocyanin, or *T. spiralis* muscle stage larval antigens; polymerized sugars, such as polydextrans; other polymers; viruses or viral subunits; and lipid-containing compounds, such as liposomes. Preferred carriers of the present invention include bacterial toxoids, such as tetanus toxoid, diphtheria toxoid, and cholera toxoid; bovine serum albumin; ovalbumin; and *T. spiralis* muscle stage larval antigens. A particularly preferred carrier is tetanus toxoid, which has been shown to be safe in vaccine applications (see, for example, Herrington et al., pp. 257–259, 1987, *Nature*, Vol. 328).

Another particularly preferred class of carriers consists of *T. spiralis* antigen carriers, defined herein as *T. spiralis* muscle stage larval antigens (as heretofore described), recombinant protein antigens corresponding to those antigens, and mimetopes of the larval antigens or corresponding recombinant protein antigens (e.g., that elicit at least some immunogenic response against trichinosis). A vaccine comprising at least one *T. spiralis* antigen carrier conjugated to a β-tyvelose-containing composition of the present invention may afford animals enhanced protection compared to either the larval antigen or composition alone.

One embodiment of the present invention is a vaccine containing more than one β-tyvelose-containing composition. Such a vaccine can also contain one or more α-tyvelose-containing compositions and/or one or more fucose-containing compositions. Although a single β-tyvelose-containing composition is sufficient to elicit an immune response, it is likely that a mixture of various types of compositions of the present invention may be more efficacious. Preferably the various types of compositions of the present invention are conjugated to effective carriers, as heretofore described. Vaccines comprising mixtures of β-tyvelose-containing compositions and fucose-containing compositions are believed to enhance the ability of such vaccines to protect an animal from trichinosis. While not being bound by theory, it is believed that the prevalence of fucose and β-tyvelose moieties as non-reducing terminal residues in *T. spiralis* immunodominant determinants suggests that each structure is likely to possess a dominant epitope that is able to elicit an immune response that is capable of protecting an animal from trichinosis.

It is to be noted that it is within the scope of the present invention that β-tyvelose-containing composition vaccines of the present invention can be used to protect an animal against infection by any parasite of the genus Trichinella, and even more broadly against infection by any organism, that contains β-tyvelose antigenic epitopes (i.e., epitopes that can be bound by antibodies produced upon administration of a β-tyvelose-containing composition vaccine of the present invention).

Vaccines of the present invention can also include additional antigenic compounds effective in eliciting an immune response against, for example, other stages of the Trichinella life cycle. Vaccines of the present invention can also be components of multiple vaccine preparations that include antigens targeted against more than one disease.

Vaccines of the present invention can be produced using standard techniques of carbohydrate and protein linkage technologies (see, for example, Lindberg et al., ibid.; Russell et al., pp. 95–114, 1990, *Carbohydrate Research*, Vol. 201; Svenson and Lindberg, pp. 323–335, 1979, *J. Immunol. Methods*, Vol. 25; McBroom et al., pp. 212–219, 1972, *Methods in Enzymology*, Vol. 28B). Briefly, the desired monosaccharides are produced and, as necessary for specific vaccine embodiments, joined by glycosidic linkage to form disaccharides and larger oligosaccharides. For preferred embodiments, the carbohydrate moieties are conjugated to effective carriers, preferably using reactive group linking agents. For example, one method to produce a vaccine containing β-tyvelose--N-acetylgalactosamine::tetanus toxoid includes the steps of (a) synthesizing β-tyvelose precursors, (b) joining the precursors to derivatized N-acetylgalactosamine residues, (c) joining the synthesized disaccharide to a suitable aglycone-containing reactive group, and (d) conjugating the modified disaccharide to a tetanus toxoid. One advantage of the present invention is the ease with which such carbohydrate-based vaccines can be produced on a consistent basis, particularly as compared with the time and effort required to produce recombinant protein-based vaccines. In addition, it may be particularly difficult to produce recombinant *T. spiralis* proteins having β-tyvelose-containing epitopes using conventional recombinant techniques since (a) bacteria do not glycosylate proteins and (b) no eukaryotic cells are known to the inventors that are capable of producing tyvelose, let alone β-tyvelose, except *T. spiralis*.

Compositions of the present invention for use in vaccines are preferably recovered in "substantially pure" form. As used herein, "substantially pure" refers to a purity that allows for the effective use of the vaccine without substantial negative side effects. For example, substantially pure vaccines would not elicit undesired biological reactions when administered to animals to be treated.

Vaccines of the present invention can be administered to any animal, preferably to mammals, more preferably to humans, pigs and bears, and particularly to pigs.

Vaccines are preferably formulated with a pharmaceutically acceptable excipient, such as an aqueous balanced salt solution that the animal to be vaccinated can tolerate. The vaccine can also include an immunopotentiator, such as an adjuvant or other agent that enhances the immune response of the vaccine. Suitable immunopotentiators include, but are not limited to, controlled release formulations such as polymeric matrices, capsules, microcapsules, microparticles, bolus preparations, diffusion devices, liposomes, lipospheres and transdermal delivery systems, and bacterial preparations (such as bacterial coat proteins), viruses or viral proteins (such as coat proteins), oils, esters, glycols, Freund's adjuvant, aluminum-based salts, calcium-based salts, silica, polynucleotides, gamma interferon, Ribi adjuvants (available from Ribi ImmunoChem Research, Inc., Hamilton, Mont.), and saponins and their derivatives, such as Quil A (available from Superfos Biosector A/S, Denmark).

In order to protect animals from trichinosis, a vaccine of the present invention is administered in an effective amount, wherein an "effective amount" is an amount that allows the animal to produce a sufficient immune response to protect itself from trichinosis. Vaccines of the present invention can be administered to animals prior to infection by *T. spiralis* to prevent trichinosis. Vaccines of the present invention can also be administered to animals after infection by *T. spiralis* in order to treat the disease, in which case the vaccine is acting as an immunotherapeutic agent. Vaccines of the present invention are advantageous because they are stable and are easy to use, particularly in the field. Acceptable administration protocols include individual dose size, number of doses, frequency of dose administration, and mode of administration. A suitable single dose of the vaccine is a dose that is capable of protecting an animal from trichinosis when administered one or more times over a suitable time period. A preferred single dose of the vaccine is from about 1 microgram (µg) to about 1 milligram (mg) of the vaccine per kilogram (kg) body weight of the animal. Booster vaccinations can be administered from about 2 weeks to several years after the original vaccination. Booster vaccinations are preferably administered when the immune response of the animal becomes insufficient to protect the animal from trichinosis. A preferred administration schedule is one in which from about 1 µg to about 1 mg of the vaccine per kg body weight of the animal is administered from about one to about two times over a time period of from about 2 weeks to about 12 months. Modes of administration can include, but are not limited to, subcutaneous, intradermal, intravenous, nasal, oral, transdermal and intramuscular routes.

The efficacy of a vaccine of the present invention to protect an animal from trichinosis can be tested in a variety of ways including, but not limited to, detection of protective antibodies (using, for example, diagnostic reagents of the present invention), detection of cellular immunity within the vaccinated animal, or challenge of the vaccinated animal with $T.\ spiralis$ or antigens thereof to determine whether the vaccinated animal is resistant to trichinosis.

Another embodiment of the present invention relates to the production and use of antibodies that are capable of selectively binding to $T.\ spiralis$ muscle stage larvae produced by an animal in response to administration of a vaccine of the present invention. One embodiment of the present invention is an antibody preparation capable of selectively binding to a Trichinella parasite that is produced by a process comprising: (1) administering to an animal an effective amount of a composition comprising a $\beta$-tyvelose-containing composition or mimetope thereof of the present invention; and (2) recovering antibodies produced by the animal in response to the administration to form the antibody preparation. As used herein, the step of recovery refers only to removing antibodies from a natural source but does not refer to the state of purify of the antibodies. Such an antibody preparation can be either polyclonal or monoclonal antibodies. Antibodies of the present invention can be fragments of any size that have similar selective epitope binding characteristics as the antibodies produced in response to vaccination. The present invention also includes antibody mimetopes which are compounds that mimic the ability of antibodies of the present invention to bind to $\beta$-tyvelose-containing epitopes.

Antibody preparations of the present invention, as well as mimetopes thereof, have a variety of potential uses that are within the scope of the present invention. For example, such antibodies can be used (a) as vaccines to passively immunize an animal in order to protect the animal from trichinosis, (b) as reagents in assays to detect $T.\ spiralis$ larvae or antigens thereof, and/or (c) as tools to recover $T.\ spiralis$ antigens having immunodominant determinants from a mixture of proteins and other contaminants.

Furthermore, antibodies of the present invention, including mimetopes thereof, can be used to target cytotoxic agents to $T.\ spiralis$ larvae and larval antigens in order to directly kill the larvae or cells expressing larval antigens on their cell surface. Targeting can be accomplished by conjugating (i.e., stably joining) such antibodies to the cytotoxic agents. Suitable cytotoxic agents are known to those skilled in the art and include, but are not limited to: double-chain toxins (i.e., toxins having A and B chains), such as diphtheria toxin, ricin toxin, Pseudomonas exotoxin, modeccin toxin, abrin toxin, and shiga toxin; single-chain toxins, such as pokeweed antiviral protein, $\alpha$-amanitin, and ribosome inhibiting proteins; and chemical toxins, such as melphalan, methotrexate, nitrogen mustard, doxorubicin and daunomycin. Preferred double-chain toxins are modified to include the toxic domain and translocation domain of the toxin but to lack the toxin's intrinsic cell binding domain.

One embodiment of the present invention is a diagnostic reagent effective in detecting Trichinella, and particularly $T.\ spiralis$, infection in an animal. A diagnostic reagent of the present invention includes a $\beta$-tyvelose-containing composition or mimetope thereof. As disclosed above, a $\beta$-tyvelose-containing composition of the present invention can be $\beta$-tyvelose or $\beta$-tyvelose joined through glycosidic linkage to at least one monosaccharide to form an oligosaccharide having at least one $\beta$-tyvelose terminal residue. Diagnostic reagents of the present invention, being based on the rare sugar $\beta$-tyvelose, are particularly advantageous because they exhibit great selectivity for $T.\ spiralis$ and other Trichinella parasites having $\beta$-tyvelose-containing epitopes in that they selectively bind to antibodies indicative of infection by such Trichinella parasites, and preferably by $T.\ spiralis$.

It is also within the scope of the present invention that $\beta$-tyvelose-containing diagnostic reagents of the present invention can be used to detect infections caused by other organisms having $\beta$-tyvelose antigenic epitopes, although to date it is believed by the inventors that no organisms other than those of the genus Trichinella have been identified as having $\beta$-tyvelose determinants, or epitopes.

Preferred diagnostic reagents bind to antibodies raised by the animal in response to $T.\ spiralis$ infection but do not appreciably bind to antibodies directed against agents that do not have substantial amounts of $\beta$-tyvelose-containing epitopes. Thus, diagnostic reagents of the present invention are much less likely to give false-positive or false-negative reactions than are known diagnostic reagents, such as those heretofore described. Two possible exceptions are antibodies produced in response to infection by Salmonella serogroup D microorganisms or $Y.\ pseudotuberculosis$ serogroup IV microorganisms since the antigens of these bacterial serogroups are the only antigens, other than TSL-1 antigens, known by the inventors to include tyvelose. However, since the bacterial antigens contain $\alpha$-tyvelose rather than $\beta$-tyvelose, one advantage of the present invention is that $\beta$-tyvelose-based diagnostic reagents can distinguish between Trichinella infections from infections by bacteria containing tyvelose (i.e., $\alpha$-tyvelose) epitopes. It should be noted that all diagnostic reagents based on $T.\ spiralis$ TSL-1 immunodominant determinants, regardless of whether they are antigen- or antibody-based, are vulnerable to the same potential complications (e.g., false-positive reactions). Until the present invention, such a concern was unappreciated by those skilled in the art.

Diagnostic reagents of the present invention are also advantageous because, as described above for vaccines, the $\beta$-tyvelose-containing compositions and $\beta$-tyvelose-containing compositions conjugated to effective carriers are stable, are easy to produce on a consistent basis, and are easy to use, particularly in field tests. Previous assays for trichinosis, regardless of whether they were competitive or non-competitive in nature, and whether they were based on crude or partially purified $T.\ spiralis$ larval antigen preparations, polyclonal antibodies, and/or monoclonal antibodies have been hampered by several problems, including selectivity (i.e., large numbers of false-positive or false-negative reactions), ease of preparation, and/or usefulness in field tests (reviewed in, for example, Su et al., pp. 76–82, 1991, $J.\ Parasitol.$, Vol. 77).

$\beta$-tyvelose-containing compositions used in vaccines of the present invention are also suitable for use as diagnostic reagents. As such, the method to produce $\beta$-tyvelose-containing compositions for diagnostic reagents is similar to that heretofore disclosed for the production of such compositions for vaccines. Suitable and preferred $\beta$-tyvelose-containing compositions for use as diagnostic reagents are as indicated for use in vaccines of the present invention.

One embodiment of the present invention is a diagnostic reagent in which the $\beta$-tyvelose-containing composition is conjugated to an effective carrier in such a manner as to not substantially interfere with the ability of the reagent to selectively bind to antibodies indicative of Trichinella, and particularly T. spiralis infection. Such a carrier may be useful in coating a diagnostic reagent to a surface for use in a diagnostic assay for trichinosis. The method and manner in which carriers are attached to diagnostic reagent compositions are similar to that heretofore disclosed for vaccine compositions. Suitable and preferred β-tyvelose-containing diagnostic reagents conjugated to carriers are as indicated for suitable and preferred β-tyvelose-containing compositions for use as vaccines. Suitable and preferred carriers for β-tyvelose-containing composition-based diagnostic reagents are as heretofore disclosed for β-tyvelose-containing composition-based vaccines.

One embodiment of the present invention is a diagnostic reagent containing more than one β-tyvelose-containing composition. Although a single composition is capable of selectively binding to an antibody indicative of T. spiralis infection, it is likely that a mixture of compositions may be more efficacious. Preferably the compositions are conjugated to effective carriers, as heretofore described.

Another embodiment of the present invention is a diagnostic reagent containing a racemic mixture of an α-tyvelose containing composition and a β-tyvelose-containing composition. Preferably the compositions are conjugated to effective carriers, as heretofore described. If a racemic mixture is used in an assay of the present invention, it is preferable to also include a reagent comprising a Trichinella-specific protein composition that, when used in accordance with the present invention, can discriminate T. spiralis infections from Salmonella serogroup D or Y. pseudotuberculosis serogroup IV infections. As used herein, "Trichinella-specific proteins" refer to proteins that are identical to or substantially similar to Trichinella proteins that are not expressed by the enterobacteria Salmonella or Yersinia. Trichinella-specific proteins can be identified using methods standard in the art. For example, antibodies raised against Trichinella proteins can be screened using techniques known to those skilled in the art to identify anti-Trichinella protein antibodies that do not cross-react with Salmonella or Yersinia (i.e., anti-Trichinella-specific antibodies). Such antibodies that recognize Trichinella-specific proteins can be used in an assay of the present invention to discriminate between Trichinella infection and infection by Salmonella serogroup D or Y. pseudotuberculosis when racemic mixtures of α-tyvelose-containing compositions and β-tyvelose-containing compositions are utilized in an initial screen. Similarly, genes encoding Trichinella proteins can be screened to identify Trichinella-specific genes that do not cross-hybridize with Salmonella or Yersinia genes under stringent hybridization conditions known to those skilled in the art. Such Trichinella-specific genes encode Trichinella-specific proteins that can be used in an assay of the present invention to discriminate between Trichinella infection and infection by Salmonella serogroup D or Y. pseudotuberculosis when racemic mixtures of α-tyvelose-containing compositions and β-tyvelose-containing compositions are utilized in the initial screen.

The present invention also includes the use of a diagnostic reagent of the present invention to detect T. spiralis infection in an animal (i.e., a method to determine T. spiralis infection in an animal using such a diagnostic reagent). Any animal susceptible to T. spiralis infection can be tested, including, but not limited to humans, pigs and bears. The detection method of the present invention is particularly useful in field tests, such as those conducted on pigs.

Any suitable assay can be used in which a diagnostic reagent of the present invention can be contacted with bodily fluid collected from an animal under conditions that allow for selective binding of the diagnostic reagent to at least one antibody in the bodily fluid to form an immunocomplex that is indicative of T. spiralis infection. As used herein, "under conditions that allow for selective binding" refers to reaction conditions, such as appropriate buffers, temperatures, and reaction times that enable selective binding of an antibody to an antigen that the antibody recognizes. Such conditions are known to those skilled in the art as are methods to optimize such conditions for a specific antigen-antibody interaction (see, for example, Sambrook et al., 1989, Molecular Cloning: A Laboratory Manual, Cold Spring Harbor Labs Press, Cold Spring Harbor, N.Y.; Su et al., J. Parasitol., ibid.). Suitable assays can include, but are not limited to, solution assays as well as solution assays including a solid phase, and can be either competitive or non-competitive. That any such assay system is suitable for determining infection is due to the advantages of the diagnostic reagent per se: that the reagent is specific (i.e., can bind to anti-Trichinella antibodies with high affinity), selective, easy to prepare, and easy to use.

A preferred method to determine Trichinella infection in an animal includes the following steps: (a) contacting bodily fluid collected from the animal with a diagnostic reagent comprising a β-tyvelose-containing composition of the present invention or mimetope thereof to forman immunocomplex and (b) determining Trichinella infection by detecting the presence of immunocomplex formed in step (a), in which the presence of the immunocomplex indicates Trichinella infection. As used herein, an "immunocomplex" refers to the complex formed when an antibody indicative of Trichinella infection binds to a diagnostic reagent of the present invention. Suitable bodily fluids to test include, but are not limited to, blood, serum, lymph, urine and cerebral spinal fluid.

Preferably, a diagnostic reagent of the present invention is bound (i.e., absorbed) to a surface. Suitable surfaces on which to coat a diagnostic reagent of the present invention include any surface to which a β-tyvelose-containing composition and/or an effective carrier can bind in an essentially stable configuration (i.e., such that the composition or carrier adsorbs to the surface and is not substantially removed from the surface during the assay). Preferably, a suitable plastic, glass, cell, or celluloid surface is used. In addition, the composition and/or carrier should be able to bind to the surface without substantially interfering with the ability of the composition to selectively bind to an antibody indicative of Trichinella infection. Examples of suitable surfaces include, but are not limited to, plate wells (e.g., in microtiter dishes), plates, dishes, tubes, beads, dip-sticks, filters (e.g., nylon, nitrocellulose, or derivatives thereof), and suitable celluloid-type matrices. Suitable assays to conduct using such surfaces include, but are not limited to, competitive or noncompetitive ELISAs (enzyme-linked immunosorbent assays), Western blots, dot blots, radioimmunoassays, immunoprecipitation assays, agglutinin assays, Ouchterlony assays, and Mancini assays. Methods to coat antigens onto surfaces are well known in the art (see, for example, Carpenter, pp. 2–9, 1992, The Manual of Clinical Laboratory Immunology, 4th Edition, Rose et al., eds., American Society of Microbiology, Washington, D.C.; Su et al., J. Parasitol., ibid.).

A number of methods known to those skilled in the art can be used to detect antigen-antibody binding interactions indicative of immunocomplexes of the present invention.

For example, the actual binding reaction can be monitored by following changes in the configurations of the antigen and antibody, for instance by noting changes in electrical potential. The complex can also be identified using a compound, preferably labeled (i.e., an "identifying labeled compound"), which can selectively bind to the selective binding complex. Alternatively, a labeled compound that selectively binds to the antibody indicative of Trichinella infection while the antibody is attached to the diagnostic reagent can be used. Such a labeled compound generally binds primarily to a non-binding epitope of the antibody. As used herein, a "non-binding epitope of the antibody" is a portion of the antibody that does not include the site at which the antibody binds selectively to the diagnostic reagent. Non-binding epitopes can include, for example, the constant regions of the antibody. Examples of labeled compounds that can be used to detect selective binding complexes include, but are not limited to, secondary antibodies, such as antibodies that target antibodies of the species being tested (e.g., anti-pig antibodies in a pig assay); bacterial surface proteins that bind to antibodies, such as Protein A and Protein G; cells that interact with antibodies, such as T cells, B cells, and macrophages; eukaryotic cell surface proteins that bind to antibodies, such as Fc receptors; and complement proteins. Preferred labeled compounds include secondary antibodies, Protein A and Protein G.

A variety of tags can be used to label compounds used to detect selective binding complexes of the present invention, including, but not limited to, radioactive, enzymatic, chemiluminescent or fluorescent labels. A preferred labeled compound of the present invention is an enzyme-linked compound capable of selectively binding to a non-binding site epitope of the antibody indicative of Trichinella infection. Depending on the label used, assays to determine Trichinella infection can be either qualitative or quantitative. Detection can be accomplished using a variety of well-known techniques, depending on the assay. For example, an enzymatic assay often yields a colorimetric product that can be detected visually or by a machine such as a densitometer or a spectrophotometer.

In a preferred embodiment, selective binding immunocomplexes are detected by a method including (a) contacting an immunocomplex with a labeled compound capable of binding selectively to the immunocomplex or the antibody within the immunocomplex; and (b) determining the presence of the labeled compound, in which the presence of the labeled compound is indicative of Trichinella infection. A particularly preferred assay system is an ELISA. In one embodiment, wells of a microtiter dish are coated with a diagnostic reagent of the present invention to form a reagent-coated surface. Effective coating can be accomplished by, for example, adding the diagnostic reagent, preferably contained in a buffer, to the wells and allowing the reagent-containing buffer to incubate in the wells at about 4° C. for several hours (e.g., overnight). The buffer is then removed and a blocking agent (e.g., milk or bovine serum albumin) is added to the reagent-coated wells in order to prevent non-selective and non-specific binding. The reagent-coated wells are washed, for example with phosphate buffered saline (PBS) containing small amounts of a detergent (e.g., about 0.05% Tween) to remove excess blocking agent. The serum to be tested for antibodies indicative of Trichinella infection is then added to the reagent-coated wells and incubated at about room temperature for about 1 hour to allow antibodies indicative of infection, if present in the serum, to bind to the reagent coating the wells (i.e., to form selective binding complexes).

The wells are then washed using, for example, PBS containing Tween, to remove unbound serum material under conditions that retain the selective binding complexes attached to the wells. An enzyme-labeled secondary antibody conjugate (e.g., goat anti-pig IgG conjugated to horse radish peroxidase) is added to the wells and incubated under conditions to allow for binding between the secondary antibody and any selective binding complexes present in the wells. Excess secondary antibody is then removed (e.g., by washing with PBS containing Tween), enzyme substrate is added (e.g., 5'aminosalicyclic acid and hydrogen peroxide if the enzyme is horse radish peroxidase), and color change is monitored either visually or using, for example, a spectrophotometer or densitometer.

Another embodiment of the present invention is a diagnostic kit which includes a diagnostic reagent of the present invention and a means for detecting Trichinella infection. Suitable diagnostic reagents are heretofore disclosed. Preferably, the diagnostic reagent comprises a β-tyvelose-containing composition conjugated to an effective carrier, such as a carrier heretofore disclosed. The kit can furthermore include a surface capable of being coated by the reagent. Preferably the surface is pre-coated by the reagent. Suitable surfaces are heretofore disclosed. A preferred surface is a dip-stick, particularly for field use. The kit can also include a means for detecting the binding of an antibody indicative of Trichinella infection (i.e., an indicative antibody) to the reagent. Suitable means for detection are heretofore disclosed. One example of a means (e.g., compound) to detect an indicative antibody is a secondary antibody that is raised against the constant regions of antibodies of the species being tested and that is conjugated to an enzyme that effects a color change in the presence of a suitable substrate.

It is also to be appreciated that the present invention also includes antibodies of the present invention as diagnostic reagents and their use, both in diagnostic kits and in methods of the present invention, to detect Trichinella, and preferably T. spiralis, infection. Such antibodies can be contacted with a bodily fluid from an animal in such a manner as to permit the formation of immunocomplexes between β-tyvelose determinants in the bodily fluid and the antibody diagnostic reagents. Such immunocomplexes can be measured using techniques similar to those described above, except as modified for the embodiment that antibodies rather than antigens are the diagnostic reagents. Such modifications can be made by those skilled in the art.

In accordance with the present invention, a therapeutic agent capable of inhibiting a Trichinella enzyme of the β-tyvelose biosynthetic pathway can be designed that is much safer and more effective than anthelminthic drugs currently available for use in treating trichinosis. Furthermore, apparently unlike current anthelminthic drugs, a therapeutic agent of the present invention can be used for prophylaxis as well as treatment. Design of such drugs is based upon the discovery that β-tyvelose is found on T. spiralis larvae and upon the assumption that the presence of β-tyvelose on Trichinella larvae and ES products is important physiologically to the parasite. In other words, if the parasite were unable to produce β-tyvelose, the parasite would die or fail to prosper.

Without being bound by theory, it is believed that tyvelose may play an important role in the physiology of the host-parasite relationship since the tyvelose-containing epitope is conserved among T. spiralis isolates despite significant differences in nucleic acid sequences between isolates. Furthermore, it has been reported that ascarosides, which are composed of the 3,6-dideoxyhexose ascarylose joined to an alcohol, are important in maintaining the toughness and impermeability of Ascaris eggs to, for example, chemicals and in preventing eggs from desiccating (see, for example, Fairbairn et al., pp. 130–134, 1955, *Can. J. Biochem. Physiol.*, Vol. 33; Fairbairn, pp. 491–554, 1957, *Exp. Parasitol.*, Vol. 6).

A therapeutic agent of the present invention preferably inhibits the biosynthesis of β-tyvelose, preferably by being targeted against Trichinella enzymes that are essentially specific to β-tyvelose biosynthesis (i.e., enzymes involved in the biosynthesis of β-tyvelose but essentially not involved in the synthesis of compounds produced by mammals). Since mammals do not produce β-tyvelose and, thus, would be unlikely to produce proteins specific to β-tyvelose biosynthesis, it is believed that such drugs will be selectively targeted to Trichinella and, as such, will have substantially insignificant, if any, negative side effects.

Preferred therapeutic agents of the present invention can be produced in a variety of ways, including the following method: (a) enzymes that are essentially specific to β-tyvelose biosynthesis in Trichinella are identified; and (b) drugs are identified and/or synthesized that inhibit the activity of such enzymes, thereby inhibiting β-tyvelose production.

Several reports describe the pathways by which β-tyvelose and other 3,6-dideoxyhexoses are synthesized by, for example, *Salmonella* and *Y. pseudotuberculosis* (see, for example, Thorson et al., pp. 5827–5828, 1993, *J. Am. Chem. Soc.*, Vol. 115; Matsuhashi et al., pp. 4267–4274, 1966, *J. Biol. Chem.*, Vol. 241; Matsuhashi, pp. 4275–4282, 1966, *J. Biol. Chem.*, Vol. 241; Matsuhashi et al., pp. 4283–4287, 1966, *J. Biol. Chem.*, Vol. 241; Hey et al., pp. 5473–5478, 1966, *J. Biol. Chem.*, Vol. 241; and references included therein), and genes encoding at least these of enzymes have been isolated from Salmonella strains (see, for example, Wyk et al., pp. 5687–5693, 1989, *J. Bacteriol.*, Vol. 171; Verma et al., pp. 5694–5701, 1989, *J. Bacteriol.*, Vol. 171). Furthermore, ascarylose appears to be synthesized in a similar manner by Ascaris (Jezyk et al., pp. 707–719, 1967, *Comp. Biochem. Physiol.*, Vol. 23). Thus, at least some *T. spiralis* enzymes specific to β-tyvelose synthesis may be identified, for example, by isolating enzymes similar to those used by bacteria and Ascaris to produce 3,6-dideoxyhexoses.

Once *T. spiralis* enzymes essentially specific to β-tyvelose biosynthesis have been identified, potential agents can be identified and produced that inhibit β-tyvelose biosynthesis, for example, by a screening program of organic molecules to identify those that specifically inhibit activity of the enzyme or by rational drug design in which, for example, the active site of the enzyme is identified and a drug designed that would interfere with the active site.

Therapeutic agents of the present invention can be administered in effective amounts to animals in order to protect animals from Trichinella infection, more particularly, trichinosis. Effective amounts and dosing regimens can be determined using techniques known to those skilled in the art. It is also within the scope of the present invention that a therapeutic agent of the present invention can also be used to treat infection by any organism, including any Trichinella parasite, having tyvelose-containing antigenic epitopes.

The following examples are provided for the purposes of illustration and are not intended to limit the scope of the invention.

EXAMPLES

Example 1

This example describes the identification of monosaccharide compositions of *T. spiralis* muscle larval antigens, including TSL-1 antigens, $L_1$ larval homogenates, and $L_1$ ES (excretory/secretory) products.

*T. spiralis* $L_1$ larval homogenates, TSL-1 antigens (i.e., Tsp 130 immunoaffinity-purified group II antigens), preparations enriched for a 43 kd TSL-1 antigen, and ES antigens were prepared as described in Denkers et al., *J. Immunol.*, ibid., and Denkers et al., *Mol. Biochem. Parasitol.*, ibid.

Total monosaccharide compositions of the larval homogenate, TSL-1 antigens, and ES antigens were determined by gas chromatography/mass spectrometry (GC/MS) of both the trimethylsilyl (TMS) ethers of methyl glycosides and of the alditol acetate derivatives of the glycosyl residues. TMS methyl glycosides were prepared by acidic methanolysis, re-N-acetylation, and trimethylsilylation. The general procedure for analysis of carbohydrate components of glycoproteins described by Chaplin, pp. 336–341, 1982, *Anal. Biochem.*, Vol. 123, was used, with the following modifications: (a) scylloinositol (2 nanomoles) was used as the internal standard; (b) samples were dried (e.g., in a SpeedVac Concentrator SVC100H, available from Savant Instruments Inc., Farmingdale, N.Y. in 1.0 milliliter (ml) Reacti-Vials (available from Pierce, Rockford, Ill.); (c) acidic methanolysis was conducted by adding 40 microliters (μl) of 3M methanolic HCl (available from Supelco, Bellefonte, Pa.) and 10 μl methyl acetate (available from Aldrich, Milwaukee, Wis.), sealing the vial with a teflon-lined septa in an open-top screw cap (available from Pierce), vortexing, and heating to about 70° C. for about 4 hours; (d) trimethylsilylation was achieved by adding 20 μl Sylon HTP (available from Supelco), vortexing, and heating to about 70° C. for about 20 minutes.

Dry derivatized samples were dissolved in HPLC-grade hexanes and the insoluble salts were allowed to settle. A portion of the clear hexane-extracted sample was analyzed by GC/MS on a gas chromatograph connected to a mass selective detector (e.g., Hewlett-Packard (HP) 5980 gas chromatograph and HP 5970 mass selective detector, each available from Hewlett-Packard, Palo Alto, Calif.). Samples were injected in the spitless mode, using, for example an HP 12-m HP-1 column and dry oxygen-free helium as the carrier gas. The oven was programmed to hold at about 80° C. for about 1 minute followed by an about 30° C. per minute rise to about 100° C., an about 10° C. per minute rise to about 265° C., an about 5 minute hold at about 265° C., and a final about 2 minute hold at about 280° C. The mass spectrometer was set to scan from mass to charge ratio (m/z) about 50 to about 800 atomic mass units (amu) at about 0.81 scans/second. TMS-derivatives were identified by both characteristic retention times and mass spectra electron impact fragmentation patterns compared to those of authentic standards. Quantitation was achieved by integration of specific ion peak areas (m/z 204—pentoses and hexoses; m/z 173—hexosamines; m/z 318—inositols) with response factors calculated from known concentrations of standards prepared under identical conditions as the samples. Standards included: xylose, rhamnose, fucose, mannose, galactose, glucose, scyllo-inositol, myo-inositol, N-acetylgalactosamine (galNAc), N-acetylglucosamine (glcNAc), N-acetylneuraminic acid, *S. typhimurium* lipopolysaccharide (LPS), *S. enteritidis* LPS, and *E. coli* LPS serotype O55:B5, all of which are available from Sigma Chemical Co., St. Louis, Mo.; chemically synthesized methyl tyvelose, methyl abequose, and methyl paratose were obtained from Dr. D. R. Bundle, Division of Biological Sciences, National Research Council of Canada, Ottawa, Ontario, Canada; and *Ascaris suum* eggs containing ascarylose were obtained from infected pigs.

Alditol acetate derivatives were prepared by trifluoroacetic acid (available from Pierce) hydrolysis of the antigen samples, followed by sodium borohydride or borodeuteride (each available from Sigma) reduction and acetylation. The general procedure for formation of the alditol acetate derivatives described in York et al., pp. 3–40, 1986, *Methods Enzymol.*, Vol. 118, as modified by Waeghe et al., pp. 281–304, 1983, *Carbohyd. Res.*, Vol. 123, for analysis of small amounts of samples, was used. Further modifications included: (a) scyllo-inositol (2 nanomoles) as the internal standard; (b) O-acetylation of the alditols by addition of 100 µl acetic anhydride (available from Supelco) and heating to about 121° C. for about 1 hour; and (c) partitioning of the per-O-acetylated alditols between about 1 ml chloroform and about 1 ml water. Dry samples were dissolved in acetone, and a portion was applied to the GC/MS as above. The oven was programmed to hold at about 50° C. for about 1 minutes, followed by an about 30° C. per minute rise to about 165° C. and an about 10° C. per minute rise to about 280° C., with a final about 2 minute hold at about 280° C. The mass spectrometer was set to scan from m/z about 80 to about 450 amu at about 1.48 scans/second.

A 3,6-dideoxyhexose, which was not seen as the TMS-methyl glycoside, was identified by alditol acetate derivation. To quantitate this sugar, equal amounts of fucose and chemically synthesized methyl tyvelose were subjected to alditol acetate derivatization, and the peak area ratio was calculated. This response factor was used to quantitate the amount of 3,6-dideoxyhexose in the *T. spiralis* samples based on the amount of fucose in both the trimethylsilyl and alditol acetate preparations.

The glycosyl compositions of the Tsp 130 immunoaffinity-purified TSL-1 antigen, ES antigens and muscle stage larval homogenate are shown in Table 1.

TABLE 1

Glycosyl compositions of *T. spiralis* muscle stage larval antigens

| | TSL-1 antigens[a] | ES antigens[a] | Larval homogenate[a] |
|---|---|---|---|
| tyvelose[b] | 24 | 21 | 8 |
| fucose | 36 | 19 | 12 |
| xylose | 0 | 1 | 1 |
| mannose | 22 | 17 | 19 |
| galactose | 0.5 | 2 | 2 |
| glucose | 1 | 4 | 19 |
| galNAc | 9 | 15 | 13 |
| glcNAc | 7 | 21 | 25 |
| myo-inositol | 0.5 | 0 | 1 |
| sialic acid | 0 | 0 | 0 |

[a]mean of 4 values obtained from 2 separate GC/MS analyses on each of 2 different antigen preparations of TSL-1 antigens, ES antigens, and larval homogenate. Values are molar percentages of total glycosyl residues found.
[b]3,6-dideoxy-D-arabinohexose All sugars listed, with the exception of the 3,6-dideoxyhexose, were identified by retention time and mass spectra following methanolysis, re-N-acetylation, and trimethylsilylation, and quantitated based on peak area. The 3,6-dideoxyhexose was detected only as the alditol acetate derivative. It was not found as the trimethylsilyl derivatized methyl glycoside, nor as any other TMS derivative (i.e., trimethylsilyl butyl glycoside).

The glycosyl composition of the TSL-1 fraction was surprising in two respects: (a) fucose accounted for about 36 molar percent of the total glycosyl residues; and (b) a 3,6-dideoxyhexose was identified, which accounted for at least about 24 molar percent of the glycosyl residues. The 3,6-dideoxyhexose also was found in preparations greatly enriched for the 43-kd TSL-1 glycoprotein antigen. Similar to the TSL-1 antigens, the glycosyl composition of the ES antigens was shown to have large amounts of fucose (about 19%) and 3,6-dideoxyhexose (about 21%). In addition, the ES antigens were comprised largely of hexosamines (about 15% N-acetylgalactosamine and about 21% N-acetylglucosamine). The crude larval homogenate also had relatively high amounts of fucose (about 12%) and hexosamines (about 13% N-acetylgalactosamine and about 25% N-acetylglucosamine), while the 3,6-dideoxyhexose was found in lower amounts (about 8%) compared to the TSL-1 and ES antigens.

Example 2

This example indicates that the *T. spiralis* 3,6-dideoxyhexose identified in Example 1 is 3,6-dideoxyarabinohexose.

Identification of the *T. spiralis* 3,6-dideoxyhexose relative configuration was achieved by comparing GC retention times of various per-O-acetylated bacterial and parasitic 3,6-dideoxyhexoses after conversion to alditol acetate derivatives. Chemically synthesized standards included methyl tyvelose (3,6-dideoxy-D-arabinohexose), methyl abequose (3,6-dideoxy-D-xylohexose), and methyl paratose (3,6-dideoxy-D-ribohexose). In addition, acid hydrolysates of biological materials containing 3,6-dideoxyhexoses were used, including colitose (3,6-dideoxy-L-xylohexose) released from *E. coli* LPS, abequose (3,6-dideoxy-D-xylohexose) released from *S. typhimurium* LPS, tyvelose (3,6-dideoxy-D-arabinohexose) released from *S. enteritidis* LPS, and ascarylose (3,6-dideoxy-L-arabinohexose) released from decoated *Ascaris suum* eggs. The identification of relative configuration was verified by co-injection with authentic standards.

The alditol acetate derivative of the TSL-1 and ES 3,6-dideoxyhexose showed the same chromatographic mobility and mass spectrum as the alditol acetate derivatives of standards containing 3,6-dideoxyarabinohexose. On the non-chiral GC column, D- and L-alditol acetate enantiomers necessarily co-elute. In contrast, the alditol acetate derivatives prepared from chemically synthesized methyl paratose, chemically synthesized methyl abequose, from abequose released from *S. typhimurium*, and from colitose released from *E. coli* all had identical mass spectra but were chromatographically distinguishable. Both the ribo and xylo 3,6-dideoxyhexose derivatives eluted later than the arabino 3,6-dideoxyhexose derivatives, suggesting that the TSL-1 3,6-dideoxyhexose was of the arabino configuration.

Example 3

This example indicates that the *T. spiralis* 3,6-dideoxyhexose identified in Example 1 is 3,6-dideoxy-D-arabinohexose (i.e., tyvelose).

Assignment of the absolute configuration of the TSL-1 and ES 3,6-dideoxyhexose was achieved by GC/MS analysis of the acetylated glycosides formed from chiral 2-octanol. 3M HCl in both (−)-2 and (+)-2 octanol (available from Sigma) were prepared by the dropwise addition of about 256 µl acetyl chloride (available from Mallinckrodt, Inc., Paris, Ky.) to about 1.2 ml octanol. Derivatizations of TSL-1 and ES antigens were achieved by: (a) hydrolysis in 2M TFA at about 121° C. for about 1 hour (hr); (b) octanolysis in either (−)-2 or (+)-2 3M octanol HCl at about 80° C. for about 3 hr; (c) addition of sodium acetate; and (d) acetylation in acetic anhydride at about 100° C. for about 1 hr. The acetylated octyl glycosides were partitioned into the organic phase between about 1 ml chloroform and about 1 ml water, dried, and extracted into acetone (see, for example, Leontein et al., pp. 359–362, 1978, *Carbohyd. Res.*, Vol. 62). Samples were analyzed by GC/MS as above for alditol acetates (total ion chromatogram) or in the selected ion monitoring mode (selecting m/z's of about 83, 85, 112,145, and 215). Methyl tyvelose (3,6-dideoxy-D-arabinohexose) and Ascaris suum eggs (containing 3,6-dideoxy-L-arabinohexose) were also subjected to hydrolysis, (−)-2 and (+)-2 octanolysis, and acetylation. GC/MS data from the resulting acetylated 3,6-dideoxyarabinohexose octyl glycoside derivatives were compared to those obtained from the TSL-1 and ES antigen samples. Verification of absolute configuration was achieved by co-injection.

The absolute configuration of the *T. spiralis* 3,6-dideoxyarabinohexose was identified as D- on the basis of retention time and mass spectra of the acetylated, optically pure, 2-octyl glycosides. Both the acetylated (−)-2 and (+)-2 octyl glycosides of TSL-1 3,6-dideoxyarabinohexose from TSL-1 and ES co-eluted with the corresponding acetylated (−)-2 and (+)-2 octyl glycosides derived from chemically synthesized tyvelose (3,6-dideoxy-D-arabinohexose). Correspondingly, as required, the acetylated (−)-2 and (+)-2 octyl glycosides of TSL-1 3,6-dideoxyarabinohexose co-eluted with their respective enantiomers, namely the acetylated (+)-2 and (−)-2 octyl glycoside derivatives of ascarylose (3,6-dideoxy-L-arabinohexose) derived from Ascaris suum eggs. Therefore, the *T. spiralis* sugar was designated as 3,6-dideoxy-D-arabinohexose (tyvelose) on the basis of the determination of relative configuration by alditol acetate derivatization and of the determination of absolute configuration by acetylation of the chiral octyl glycosides.

Example 4

This example demonstrates determination of the glycosyl composition of TSL-1 carbohydrates.

TSL-1 antigens (670 µg protein) were buffer exchanged from PBS/NaN$_3$ into 18 megaohm Milli-Q (available from Millipore Corp., Bedford Mass.) by centrifugation at 5000×g in a BSA-passivated Centriprep C-10 (available from Amicon, Danvers, Mass.). The carbohydrates were then treated with about 100 µl 1M NaBD$_4$ in 50 mM NaOH at about 45° C. for about 20 hr to β-eliminate and reduce O-glycosidically-linked oligosaccharides. Following addition of glacial acetic acid and evaporation, the sample was redissolved and evaporated in 10% acetic acid in methanol (about 3 times) and in absolute methanol (about 3 times). The sample was then desalted by cation exchange column chromatography (330 µl BioRad (Hercules, Calif.) AG50W-X8 resin, H+ form, 1.7 meq/ml, packed on a 5 mm silanized glass wool plug in a 5¾ inch silanized Pasteur pipet). The carbohydrates were eluted with Milli-Q water until the pH of the eluate became neutral. The eluate was concentrated to about 0.5 ml, transferred to a 1.0 ml Reacti-Vial, and dried to completion. TSL-1 carbohydrate antigens were methylated by the Hakomori procedure (see, Hakomori, pp. 205–208, 1964, *J. Biochem.* (Tokyo), Vol. 55), as adapted by Sandford and Conrad (see, Sandford et al., pp. 1508–1517, 1966, *Biochem.*, Vol. 5) and as modified for microanalysis by Waeghe et al., ibid. The sample was initially dissolved in about 250 µl dry dimethylsulfoxide (available from Pierce), with continuous stirring for about 2 hr at room temperature. About 20 µl of 4.5M sodium dimethylsulfinyl carbanion (see, for example, York et al., ibid.; Stellner et al., pp. 464–472, 1973, *Arch. Biochem. Biophys.*, Vol. 155) was added, and the reaction mixture was stirred for about 2 hr at room temperature. About 35 µl of methyl iodide (available from Aldrich) was added dropwise, and the mixture was stirred for 12 hr at room temperature. The reaction mixture was diluted with water to obtain a 1:1 (v:v) dimethyl sulfoxide:water solution, and the pre-reduced, per-O-methylated carbohydrates were recovered and purified by reverse-phase chromatography on a Sep-Pak C-18 cartridge (available from Waters Associates, Inc., Milford, Mass.) (see Waeghe et al., ibid.). The final two elution fractions (2 ml 100% acetonitrile for per-O-methylated alditols d.p. 2–10; 4 ml 100% EtOH for per-O-methylated alditols of larger oligosaccharides d.p.>10 and polysaccharides) were collected in 13×100 mm test tubes and the solvent was evaporated to dryness using a stream of filtered air at room temperature. The per-O-methylated carbohydrates were converted into their partially O-acetylated, partially O-methylated alditols by hydrolysis in 2M TFA, reduction with NaBD$_4$, and acetylation with acetic anhydride (York et al., ibid.). Glycosyl linkage composition was determined by GC/MS of the partially O-acetylated, partially O-methylated alditols using the temperature program as described for alditol acetates. The hexosamine residues were identified by comparing retention times and mass spectra to undermethylated N-acetylglucosamine and N-acetylgalactosamine standards. Verification of these designations was achieved by co-injection.

Results from the characterization of TSL-1 glycosyl linkages as determined by Hakomori methylation of the TSL-1 antigens are shown in Table 2.

TABLE 2

Glycosyl linkage composition of TSL-1 carbohydrates

| Sugar | Mole percent |
| --- | --- |
| t-tyvelose[a,b] | 8.8 |
| t-fucose[b] | 13.8 |
| t-mannose | 1.9 |
| 3,4-fucose | 2.7 |
| 2-mannose | 3.9 |
| 2,4-mannose | 7.6 |
| 2,6-mannose | 5.5 |
| 3,6-mannose | 10.1 |
| 4-glcNAc[c] | 9.7 |
| 3-galNAc[c] | 14.5 |
| 3,4-glcNAc[c] | 21.4 |

[a]3,6-dideoxy-D-arabinohexose
[b]the yields of t-tyvelose and t-fucose were lower than would be expected, presumably due to their acid-liability and/or volatility
[c]hexosamines identified by comparing retention times and mass spectra to undermethylated N-acetylglucosamine and N-acetylgalactosamine standards The TSL-1 3,6-dideoxy-D-arabinohexose was found to be present entirely as non-reducing terminal residues. Approximately 83% of the fucose was also present as non-reducing terminal residues, with the remaining fucose found as 3,4-linked branched residues. The mannosyl derivatives found included terminal, 2-linked, 2,4-linked, 2,6-linked, and 3,6-linked residues. Because the entire TSL-1 sample was methylated without first separating N- and O-linked sugars, it is probable that these residues may be constituents of both N-linked and O-linked glycoproteins.

Example 5

This example demonstrates that a β-tyvelose-containing composition of the present invention, namely β-tyvelose--N-acetylgalactosamine, competes with *T. spiralis* immunoaffinity-purified muscle stage larval antigens (i.e., TSL-1 antigens) for binding to monoclonal antibody Tsp 130, a monoclonal antibody that selectively binds to the immunodominant determinant of TSL-1 antigens.

Monoclonal antibody Tsp 130 was prepared as described in Denkers et al. (*J. Immunol.* 144:3152–3159, 1990). TSL-1 antigens were prepared from muscle stage larvae by affinity purification using a Tsp 130 antibody preparation and methods as described in Denkers et al., *J. Immunol.*, ibid., and Denkers et al., *Mol. Biochem. Parasitol.*, ibid.

Wells in an ELISA plate were coated with TSL-1 antigens as follows. A 96-well Immunlon II ELISA plate, available from Dynatech Laboratories, Chantilly, Va., was coated with about 100 µl/well of a solution containing about 15 ng of TSL-1 antigens per 100 µl carbonate buffer at pH 9.6, overnight, at about 4° C. Following the overnight incubation, the TSL-1 antigen-containing solution was discarded from the wells of the ELISA plate. No wash was performed. The wells of the ELISA plate were then filled to the top with about 10% dry milk in phosphate buffered saline and allowed to incubate for about 1 hour at room temperature. Following the 1 hour incubation, the milk solution was discarded from the wells. No wash was performed.

Samples in which Tsp-130 monoclonal antibodies and disaccharides, as listed below, were pre-incubated prior to addition to the treated ELISA plate were prepared as follows. One thousand-fold serial dilutions of the following disaccharides, ranging from about $1 \times 10^{-6}$ fg/ml to about 1 mg/ml, were prepared in water: (a) α-tyvelose(1,3)β-d-N-acetylgalactosamine (also referred to herein as α-tyv-GalNAc); (b) β-tyvelose(1,3)β-d-N-acetylgalactosamine (also referred to herein as β-tyv-GalNAc); and (c) α-glucoseα-D-glucose (also referred to herein as α-glc-glc, or trehalose). The disaccharide-containing serial dilutions were then mixed with an about 1:6,400 dilution of Tsp 130 antibody at an about 1:1 (v:v) ratio. The samples were incubated for overnight at about 4° C.

About 100 µl of the pre-incubation samples were added in triplicate to wells in the milk-coated ELISA plate. The plate was incubated for about 1 hour at room temperature to allow any unbound Tsp 130 antibody in each sample to bind to TSL-1 antigen coated onto the ELISA plate. The plate was then washed 3 times with water.

The amount of Tsp 130 antibody that bound to TSL-1 antigen coated onto the ELISA plate was determined using the following method. About 100 µl of an about 1:8,000 dilution of horse radish peroxidase-conjugated goat anti-mouse IgG antibody (available from Kirkegaard & Perry Laboratories, Inc., Gaithersburg, Md.) was added to each well of the ELISA plate. The plate was then incubated for about 45 minutes at room temperature. Following incubation, the plate was washed 5 times with 0.05% Tween 20 in phosphate-buffered saline (PBS). The peroxidase-conjugated antibodies which bound to Tsp 130 antibody in the wells were then detected by (a) adding 100 µl/well of 3,3',5,5'-tetramethylbenzidine mixed 1:1 (v:v) with 0.02% hydrogen peroxide in a citric acid buffer (i.e., TMB Microwell Peroxidase Substrate System available from Kirkegaard & Perry) and (b) incubating the plate for about 5 minutes at room temperature. The color reaction was stopped by adding about 100 µl/well of 1M o-phosphoric acid. The color reaction was quantitated using a Microplate Reader #7520, available from Cambridge Technology, Inc., Watertown, Mass. at a wavelength of 450 nm.

Analysis of the results of the competition ELISA test indicated that about 500 µg/ml of β-tyv-GalNAc inhibited binding of Tsp 130 antibody to TSL-1 antigen by about 100%; that about 500 µg/ml of α-tyv-GalNAc inhibited binding of Tsp 130 antibody to TSL-1 antigen by about 50%; and that about 500 µg/ml of α-glc-glc inhibited binding of Tsp 130 antibody to TSL-1 antigen by about 30%. Thus, monoclonal antibody Tsp 130 binds to β-tyv-GalNAc with a higher affinity than to α-tyv-GalNAc. The affinity of binding between monoclonal antibody Tsp 130 and α-glc-glc is even weaker.

Example 6

This example also demonstrates that the β-tyvelose-containing composition β-tyvelose-N-acetylgalactosamine competes with *T. spiralis* immunoaffinity-purified muscle stage larval antigens for binding to Tsp 130 monoclonal antibody.

A competitive inhibition assay was performed as described in Example 5 with the following variation. Pre-incubation samples were prepared in which 100-fold dilutions of α-tyv-GalNAc and β-tyv-GalNAc, respectively, ranging from about 2 fg/ml to about 2 mg/ml of each disaccharide, were mixed with an about 1:6,400 dilution of Tsp 130 antibody at an about 1:1 (v:v) ratio and incubated as described in Example 5. The final concentration of sugar in the samples ranged from about 1 fg/ml to about 1 mg/ml, and the final concentration of Tsp antibody in each sample was about 1:12,800.

Analysis of the results of this study indicated that about 1 mg/ml of β-tyv-GalNAc inhibited Tsp 130 binding to TSL-1 antigen by about 97% and that about 100 µg/ml of β-tyv-GalNAc inhibited Tsp 130 binding to TSL-1 antigen by about 92%. The results also indicated that 1 mg/ml of α-tyv-GalNAc inhibited Tsp 130 binding to TSL-1 antigen by about 74%. Thus, as in Example 5, monoclonal antibody Tsp 130 binds to β-tyv-GalNAc with a higher affinity than to α-tyv-GalNAc.

Example 7

This example demonstrates that a β-tyvelose-containing composition of the present invention, namely β-tyvelose-N-acetylgalactosamine, competes with a crude *T. spiralis* muscle stage larval lysate for binding to monoclonal antibody Tsp 130.

Monoclonal antibody Tsp 130 was prepared as described in Example 5. A crude muscle larval lysate of *T. spiralis*, referred to herein as E11.5, was prepared according to the method as described in Reason et al., ibid.

An Immunlon II ELISA plate coated with E11.5 lysate was prepared using the method described in Example 5 with the variation that wells in the plate were coated with about 100 µl/well of a solution containing about 250 ng of E11.5 lysate per 100 µl carbonate buffer at pH 9.6. Pre-incubation samples were prepared as described in Example 5, and the competitive inhibition assay was conducted as described in Example 5.

Analysis of the results of this study indicated that about 500 µg/ml of β-tyv-GalNAc inhibited Tsp 130 binding to the crude *T. spiralis* muscle stage larval lysate E11.5 by about 97%, while about 500 µg/ml of α-tyv-GalNAc inhibited Tsp 130 binding to E11.5 lysate by about 28%. The results also indicated that about 500 µg/ml of α-glc-glc inhibited Tsp 130 binding to E11.5 lysate by about 7%. Thus, these results indicate that monoclonal antibody Tsp 130 binds to β-tyv-GalNAc with a higher affinity than to α-tyv-GalNAc or to α-glc-glc.

Taken together, the results of Examples 5 through 7 indicate that β-tyvelose competitively inhibits the binding of Tsp 130 antibody to *T. spiralis* TSL-1 antigens and E11.5 lysate better than α-tyvelose and even better than α-glc-glc. Thus, in Trichinella, β-tyvelose is a more immunodominant carbohydrate epitope than α-tyvelose. It should be noted, however, that α-tyvelose is able to competitively inhibit Tsp 130 antibody binding to TSL-1 antigen but at a higher concentration than β-tyvelose.

Example 8

This example demonstrates that sera isolated from pigs infected with *T. spiralis*, (i.e., *T. spiralis*-infected pig sera) contain antibodies specific for TSL-1 antigens that are specific for the same TSL-1 epitope as recognized by monoclonal antibody Tsp 130.

In a first experiment, the ability of Tsp 130 antibody, compared with a non-specific purified mouse IgG antibody, to inhibit the binding of antibodies contained in *T. spiralis* infected pig sera to TSL-1 antigens was tested in a competition ELISA. Monoclonal antibody Tsp 130 was prepared as described in Example 5. Wells in an ELISA plate were coated with TSL-1 antigens as described in Example 5. Experimental samples were prepared by mixing a constant concentration of *T. spiralis*-infected pig sera (1:250 dilution of pig sera #223 obtained 6 weeks post-infection with *T. spiralis*) with increasing concentrations of Tsp 130 antibody as shown in Table 3. Control samples were prepared by mixing the same concentration of *T. spiralis*-infected pig sera as described for experimental samples with increasing concentrations of purified mouse IgG antibody (available from Pierce, Rockford, Ill.) as shown in Table 3.

The experimental and control samples were added in triplicate to the TSL-1-coated ELISA plate and the plate incubated and washed using the method described in Example 5. The amount of pig antibody bound to the TSL-1 antigens coated onto the ELISA plate was determined by adding about 100 μl/well of an about 1:300 dilution of horse radish peroxidase-conjugated goat anti-swine IgG antibody (available from Kirkegaard & Perry Laboratories, Inc.) to each well of the ELISA plate. The plate was then incubated for about 45 minutes at room temperature. Following incubation, the plate was washed and the amount of horseradish peroxidase-conjugated antibody bound to the ELISA plate was detected using the method described in Example 5. Results from the competition assays are shown in Table 3 below.

TABLE 3

| Inhibition of *T. spiralis*-infected #223 pig sera binding to TSL-1 antigen by Tsp 130 antibody or purified mouse IgG antibody. | | | |
|---|---|---|---|
| Tsp 130 (concentration) | % inhibition by pig #223 sera | mouse IgG (concentration) | % inhibition by pig #223 sera |
| 4.6 μg/ml | 91 | 5.5 μg/ml | 4 |
| 2.3 | 86 | 2.75 | 7 |
| 1.15 | 82 | 1.38 | 0 |
| 575 ng/ml | 73 | 688 ng/ml | 11 |
| 288 | 67 | 344 | 7 |
| 144 | 49 | 172 | 1 |
| 72 | 32 | 86 | 0 |
| 36 | 19 | 43 | 8 |
| 18 | 24 | 21 | 11 |
| 9 | 17 | 11 | 3 |

In a second experiment, the ability of Tsp 130 antibody to inhibit the binding of antibodies contained in pig sera isolated from two different pigs (pig #217 and pig #223, sera collected 12 and 6 weeks, respectively, post *T. spiralis* infection) infected with *T. spiralis* was tested in competition assays as described immediately above. The concentration of Tsp 130 antibody used in the competition assay and the results of the assays are shown in Table 4.

TABLE 4

| Inhibition of *T. spiralis* infected #217 or #223 pig sera binding to TSL-1 antigen by Tsp 130 antibody. | | |
|---|---|---|
| Tsp 130 (concentration) | % inhibition by pig #217 sera | % inhibition by pig #223 sera |
| 4.6 μg/ml | 50 | 60 |
| 2.3 | 50 | 61 |
| 1.15 | 40 | 34 |
| 575 ng/ml | 31 | 21 |
| 288 | 29 | 23 |
| 144 | 24 | 14 |
| 72 | 32 | 11 |
| 36 | 33 | 15 |
| 18 | 34 | 19 |
| 9 | 37 | 6 |

In a separate experiment, sera collected from pig #217 and pig #223 prior to *T. spiralis* infection (i.e., pre-infected sera) do not bind to TSL-1 antigens when tested in direct-binding ELISA's using the methods and horseradish peroxidase-conjugated anti-swine IgG antibody described above.

Analysis of the results of the competition ELISA tests shown in Tables 3 and 4 indicated that detectable amounts of anti-TSL-1 antibodies were present in sera isolated from pig and pig #223 after the pigs had been infected with *T. spiralis*. The detected anti-TSL-1 antibodies in the infected pig sera were specific for the same epitope on TSL-1 antigen as is recognized by Tsp 130 antibody, namely a β-tyvelose-containing composition.

Example 9

This example demonstrates that a β-tyvelose-containing composition of the present invention competes with *T. spiralis* immunoaffinity-purified muscle stage larval antigens (i.e., TSL-1 antigens) for binding to pig sera isolated from pigs infected with *T. spiralis*.

Using the methods described in Example 5, wells in an ELISA plate are coated with TSL-1 antigens as described in Example 5. A competition assay is performed by pre-incubating *T. spiralis* infected pig sera with the disaccharides described in Example 5. The pre-incubation samples are added to wells in the TSL-1 antigen-coated ELISA plate and the plate is incubated and washed as described in Example 5. The amount of pig antibodies that bind to the TSL-1 antigen-coated ELISA plate is determined as described in Example 8.

The experiment indicates that the *T. spiralis* infected pig sera contain detectable levels of antibodies that are capable of binding to a β-tyvelose-containing disaccharide of the present invention. Thus, a β-tyvelose-containing composition of the present invention is useful as a diagnostic reagent for Trichinella infection.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims:

What is claimed is:

1. A diagnostic reagent to detect Trichinella infection comprising β-tyvelose joined through glycosidic linkage to at least one monosaccharide to form an oligosaccharide having at least one β-tyvelose terminal residue.

2. The reagent of claim 1, wherein said reagent is capable of detecting *T. spiralis* infection.

3. The reagent of claim 1, wherein said β-tyvelose-containing composition is conjugated to a carrier effective to present said composition for reaction with an antibody indicative of infection by a Trichinella parasite.

4. The reagent of claim 1, wherein said monosaccharide is selected from the group consisting of tyvelose, fucose, mannose, N-acetylgalactosamine, and N-acetylglucosamine.

5. The reagent of claim 1, wherein said monosaccharide joined to β-tyvelose comprises N-acetylgalactosamine.

6. The reagent of claim 1, wherein said β-tyvelose-containing composition is selected from the group consisting of a disaccharide, a trisaccharide and a tetrasaccharide.

7. The reagent of claim 1, wherein said composition comprises a racemic mixture of said β-tyvelose-containing composition and an α-tyvelose-containing composition, said α-tyvelose-containing composition being selected from the group consisting of α-tyvelose and α-tyvelose joined through glycosidic linkage to at least one monosaccharide to form an oligosaccharide having at least one α-tyvelose terminal residue.

8. A method to detect Trichinella infection in an animal comprising:

(a) contacting a bodily fluid collected from said animal with a diagnostic reagent comprising a β-tyvelose-containing composition to form an immunocomplex between said diagnostic reagent and an antibody in said bodily fluid indicative of Trichinella infection, said β-tyvelose-containing composition comprising β-tyvelose joined through glycosidic linkage to at least one monosaccharide to form an oligosaccharide having at least one β-tyvelose terminal residue; and (b) determining Trichinella infection by detecting the presence of said immunocomplex formed in step (a), wherein the presence of said immunocomplex indicates Trichinella infection.

9. The method of claim 8, wherein said reagent is capable of detecting *T. spiralis* infection.

10. The method of claim 8, wherein said β-tyvelose-containing composition is conjugated to a carrier effective to present said composition for reaction with an antibody indicative of infection by a Trichinella parasite.

11. The method of claim 8, wherein said monosaccharide in said β-tyvelose-containing composition is selected from the group consisting of tyvelose, fucose, mannose, N-acetylgalactosamine, and N-acetylglucosamine.

12. The method of claim 8, wherein said monosaccharide joined to β-tyvelose comprises N-acetylgalactosamine.

13. The method of claim 8, wherein said β-tyvelose-containing composition is selected from the group consisting of a disaccharide, a trisaccharide and a tetrasaccharide.

14. The method of claim 8, wherein said composition comprises a racemic mixture of said β-tyvelose-containing composition and an α-tyvelose-containing composition, said α-tyvelose-containing composition being selected from the group consisting of α-tyvelose and α-tyvelose joined through glycosidic linkage to at least one monosaccharide to form an oligosaccharide having at least one α-tyvelose terminal residue.

15. The method of claim 8, wherein said animal is selected from the group consisting of pigs, humans and bears.

16. The method of claim 8, wherein said step of determining comprises:

(a) contacting said immunocomplex with a labeled compound capable of binding selectively to said immunocomplex or to said antibody within said immunocomplex; and (b) determining the presence of said labeled compound, wherein presence of said labeled compound is indicative of Trichinella infection.

17. The method of claim 14, further comprising a process for discriminating between Trichinella infection and an infection caused by a microorganism selected from the group consisting of Salmonella serogroup D microorganisms, *Yersinaia pseudotuberculosis* serogroup IV microorganisms and a mixture thereof, in said animal comprising:

(a) contacting bodily fluid collected from said animal with an agent comprising at least one fucose-containing composition, said fucose-containing composition being selected from the group consisting of fucose and fucose joined through glycosidic linkage to at least one monosaccharide to form an oligosaccharide, to form an immunocomplex; and (b) determining Trichinella infection by detecting the presence of said immunocomplex formed in step (a), wherein the presence of said immunocomplex indicates Trichinella infection.

18. A diagnostic kit for detecting Trichinella infection in an animal, said kit comprising (a) a diagnostic reagent comprising β-tyvelose joined through glycosidic linkage to at least one monosaccharide to form an oligosaccharide having at least one β-tyvelose terminal residue: and (b) a means for detecting Trichinella infection.

19. The kit of claim 18, wherein said reagent is capable of detecting *T. spiralis* infection.

20. The kit of claim 18, wherein said reagent is immobilized on a substrate.

21. The kit of claim 18, wherein said means of detecting comprises a labeled substance compound capable of binding to an antibody indicative of Trichinella infection.

22. The kit of claim 18, wherein said monosaccharide in said composition is selected from the group consisting of tyvelose, fucose, mannose, N-acetylgalactosamine, and N-acetylglucosamine.

23. The kit of claim 18, wherein said monosaccharide joined to β-tyvelose comprises N-acetylgalactosamine.

24. The kit of claim 18, wherein said composition is selected from the group consisting of a disaccharide, a trisaccharide and a tetrasaccharide.

25. The kit of claim 18, wherein said composition comprises a racemic mixture of said β-tyvelose-containing composition and an α-tyvelose-containing composition, said α-tyvelose-containing composition being selected from the group consisting of α-tyvelose and α-tyvelose joined through glycosidic linkage to at least one monosaccharide to form an oligosaccharide having at least one α-tyvelose terminal residue.

* * * * *